United States Patent [19]

Itoh et al.

[11] Patent Number: 5,296,162

[45] Date of Patent: Mar. 22, 1994

[54] NEAR INFRARED ABSORBERS AND DISPLAY/RECORDING MATERIALS USING THE SAME

[75] Inventors: Hisao Itoh, Yokohama; Katashi Enomoto, Zushi; Takahisa Oguchi; Tutomu Nishizawa, both of Yokohama, all of Japan

[73] Assignees: Mitsui Toatsu Chemicals, Incorporated, Tokyo; Yamamoto Chemicals, Incorporated, Yao, both of Japan

[21] Appl. No.: 846,796

[22] Filed: Mar. 2, 1992

Related U.S. Application Data

[62] Division of Ser. No. 451,175, Dec. 15, 1989, Pat. No. 5,124,067.

[30] Foreign Application Priority Data

Dec. 15, 1988 [JP] Japan .............................. 63-314986
Jan. 13, 1989 [JP] Japan ................................. 64-4763
Jan. 13, 1989 [JP] Japan ................................. 64-4764
Apr. 19, 1989 [JP] Japan ................................ 64-97604

[51] Int. Cl.$^5$ ................... C09B 47/04; C09K 19/58
[52] U.S. Cl. .................. 252/299.2; 252/299.61; 252/587; 359/104; 359/105; 359/106; 359/358; 540/140
[58] Field of Search ............... 252/299.2, 299.61, 587; 359/104, 105, 106, 358; 540/140

[56] References Cited

U.S. PATENT DOCUMENTS

| | | | |
|---|---|---|---|
| 3,291,746 | 12/1966 | Donoian et al. | 252/587 |
| 4,039,467 | 8/1977 | Tucker | 252/587 X |
| 4,529,688 | 7/1985 | Law et al. | 430/494 |
| 4,730,902 | 3/1988 | Suzuki et al. | 252/587 X |
| 4,791,023 | 12/1988 | Suzuki et al. | 252/587 X |
| 4,960,538 | 10/1990 | Itoh et al. | 252/299.2 |
| 5,124,067 | 6/1992 | Itoh et al. | 252/299.2 |

FOREIGN PATENT DOCUMENTS

| | | |
|---|---|---|
| 0155780 | 9/1985 | European Pat. Off. |
| 0212907 | 3/1987 | European Pat. Off. |
| 0262761 | 4/1988 | European Pat. Off. |
| 0272935 | 6/1988 | European Pat. Off. |
| 0302497 | 2/1989 | European Pat. Off. |
| 2613111 | 9/1988 | France |
| 3048281 | 2/1988 | Japan .................. 540/140 |
| 2168372 | 6/1986 | United Kingdom |
| 8806175 | 8/1988 | World Int. Prop. O. |

OTHER PUBLICATIONS

Journal of the Chemical Society, Perkin Transactions I, No. 8, Aug. 1988, pp. 2453-2458, London, GB; M. J. Cook et al.: "Octa-alkoxy phthalocyanine and naphthalocyanine derivatives: dyes with Q-band absorption in the far red or near infrared".

Chemical Abstracts, vol. 106, No. 26, Jun. 29, 1987, p. 725, abstract No. 224565h, Columbus, Ohio, US; & JP-A-61197 280(TDK Corp.) Jan. 9, 1986 *Abstract*.

Chemical Abstracts, vol. 106, No. 26, Jun. 29, 1987, p. 726, abstract No. 224577p, Columbus, Ohio, US; & JP-A-61 246 091 (TDK Corp.) Jan. 11, 1986 *Abstract*.

Primary Examiner—Richard D. Lovering
Attorney, Agent, or Firm—Oblon, Spivak, McClelland, Maier & Neustadt

[57] ABSTRACT

Near infrared absorbers which have a molecular extinction coefficient of 200,000 or more and are represented by the formula (I)

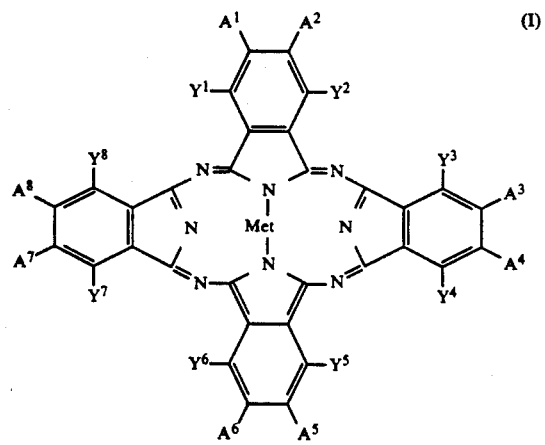

wherein each of $Y^1$, $Y^2$, $Y^3$, $Y^4$, $Y^5$, $Y^6$, $Y^7$ and $Y^8$ is hydrogen, an alkyl group, alkoxyl group or alkylthio group; each of $A^1$, $A^2$, $A^3$, $A^4$, $A^5$, $A^6$, $A^7$ and $A^8$ is hydrogen, halogen, a nitro group, alkyl group, aralkyl group, alkenyl group, alkynyl group, alkoxyl group, aryloxy group, alkylthio group or arylthio group; and Met represents two hydrogen atoms or a metal, are useful for the production of optical display and recording materials.

5 Claims, No Drawings

NEAR INFRARED ABSORBERS AND DISPLAY/RECORDING MATERIALS USING THE SAME

This is a division, of application Ser. No. 07/451,175, filed on Dec. 15, 1989, now U.S. Pat. No. 5,124,067.

BACKGROUND OF THE INVENTION

1. Field of the Invention

The present invention relates to near infrared absorbers and to optical recording media (including optical cards), filters (including spectacles) for transmission and cutoff of near infrared rays and liquid crystal display elements utilizing near infrared rays.

2. Discussion of the Background

Near infrared absorbers play an important role in the field of optoelectronics. In particular, such absorbers are useful for information recording devices, display sensors and protective spectacles.

As disclosed in Japanese Patent Laid-Open Publication Nos. 209,583/1985, 152,769/1986, 154,888/1986, 197,280/1986, 246,091/1986 and 39,286/1987, it is known to use phthalocyanines as near infrared absorbers, but the disclosed phthalocyanines are poor in absorbance, since they are liable to associate. For this reason, in the case of the optical recording media manufactured by using these phthalocyanines, the reflectance at 780 to 830 nm is low and the sensitivity is also insufficient; in the case of filters, the absorption spectrum is broad, and thus selective transmission is poor; and in the case of liquid crystal display elements, contrast is also poor.

SUMMARY OF THE INVENTION

Accordingly, it is an object of the present invention to provide novel near infrared absorbers which do not exhibit the above-mentioned drawbacks.

It is another object of the present invention to provide a method for preparing such near infrared absorbers.

It is another object of the present invention to provide optoelectronics materials prepared by using such above-mentioned near infrared absorbers.

These and other objects, which will become apparent during the course of the following detailed description, have been achieved by the inventors' discovery that novel phthalocyanine derivatives having a molecular extinction coefficient of 200,000 or more which are represented by the formula (I):

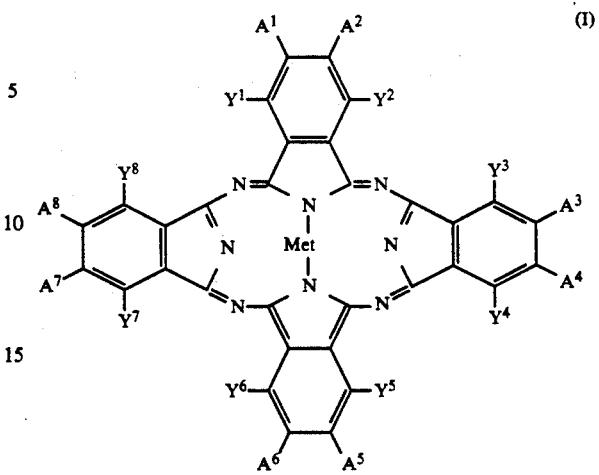

in which each of $Y^1$, $Y^2$, $Y^3$, $Y^4$, $Y^5$, $Y^6$, $Y^7$ and $Y^8$ is independently a hydrogen atom, a straight-chain or branched alkyl group having 1 to 15 carbon atoms, a straight-chain, branched or cyclic alkoxyl group having 4 to 15 carbon atoms, a straight-chain, branched or cyclic alkylthio group having 4 to 15 carbon atoms; provided that each pair of $Y^1$ and $Y^2$, $Y^3$ and $Y^4$, $Y^5$ and $Y^6$, and $Y^7$ and $Y^8$ is not a pair of hydrogen atoms, alkyl groups or alkylthio groups simultaneously, or a combination of an alkyl group and a hydrogen atom; each of $A^1$, $A^2$, $A^3$, $A^4$, $A^5$, $A^6$, $A^7$ and $A^8$ is independently a hydrogen atom, a halogen atom, a nitro group, a straight-chain, branched or cyclic alkyl group having 1 to 10 carbon atoms, an aralkyl group having 7 to 20 carbon atoms, an alkenyl group having 1 to 10 carbon atoms, an alkynyl group having 1 to 10 carbon atoms, a straight-chain or branched alkoxyl group having 1 to 4 carbon atoms or a cyclic alkoxyl group having 6 to 10 carbon atoms, an aryloxy group having 6 to 20 carbon atoms, a straight-chain, branched or cyclic alkylthio group having 1 to 10 carbon atoms or an arylthio group having 6 to 20 carbon atoms; each pair of $A^1$ and $A^2$, $A^3$ and $A^4$, $A^5$ and $A^6$, and $A^7$ and $A^8$ may be bound together so as to form a ring; provided that when all of $A^1$, $A^2$, $A^3$, $A^4$, $A^5$, $A^6$, $A^7$ and $A^8$ are hydrogen atoms and each pair of $Y^1$ and $Y^2$, $Y^3$ and $Y^4$, $Y^5$ and $Y^6$, and $Y^7$ and $Y^8$ is a combination of a hydrogen atom and an alkoxyl group, the alkoxyl group has 4 to 9 carbon atoms and is branched or cyclic; and Met represents two hydrogen atoms, a divalent metal atom, a trivalent or tetravalent substituted metal atom, or an oxymetal group, can be used as near infrared absorbers.

Furthermore, the present invention is directed to optical recording media, near infrared absorbing filters, liquid crystal display elements and optical cards manufactured by using the above-mentioned near infrared absorbers.

The present near infrared absorbers represented by the formula (I) have a sharp absorption at 700 to 900 nm and a high molecular extinction coefficient, and therefore are effective in optical recording media for use with semiconductor lasers (optical discs and optical cards), near infrared absorption filters (laser-responsive elements, outside light cutoff filters and protective spectacles), laser beam writing or transmission type liquid crystal materials and shutters.

DETAILED DESCRIPTION OF THE PREFERRED EMBODIMENTS

In the formula (I), $Y^1$, $Y^2$, $Y^3$, $Y^4$, $Y^5$, $Y^6$, $Y^7$ and $Y^8$ are groups for preventing the association between phthalocyanine molecules, and $A^1$, $A^2$, $A^3$, $A^4$, $A^5$, $A^6$, $A^7$ and $A^8$ are groups for assisting $Y^1$, $Y^2$, $Y^3$, $Y^4$, $Y^5$, $Y^6$, $Y^7$ and $Y^8$ in extending perpendicularly from the plane of the phthalocyanine ring. Therefore, on condition that the number of the carbon atoms in $Y^1$, $Y^2$, $Y^3$, $Y^4$, $Y^5$, $Y^6$, $Y^7$ and $Y^8$ is the same, the branched or cyclic type substituents tend to result in higher reflectance and refractive index than the straight-chain type.

Typical examples of the alkoxyl group represented by $Y^1$, $Y^2$, $Y^3$, $Y^4$, $Y^5$, $Y^6$, $Y^7$ and $Y^8$ include an n-butyloxy group, iso-butyloxy group, tert-butyloxy group, sec-butyloxy group, n-pentyloxy group, iso-pentyloxy group, neo-pentyloxy group, 1-methylbutyloxy group, 2-methylbutyloxy group, n-hexyloxy group, 2-ethylbutyloxy group, 3-methylpentyloxy group, 4-tert-butyl-hexyloxy group, 1,2-dimethylpropyloxy group, n-octyloxy group, n-nonyloxy group and n-dodecyloxy group. However, as groups which have great steric hindrance, easily extend perpendicularly from the plane of the phthalocyanine ring and increase the light absorption per unit weight of the near infrared absorber, as groups which enhance sensitivity when optical recording media are manufactured, and as groups which are effective to improve solubility in a spin coating solvent, examples of the particularly preferred alkoxyl groups include an iso-butyloxy group, iso-pentyloxy group, 1,2-dimethylpropyloxy group, 2-ethylbutyloxy group, 1-ethylbutyloxy group, 1-ethyl-2-methylpropyloxy group, 1-iso-propyl-2-methylpropyloxy group, 2-ethylhexyloxy group, 1-iso-propyl-3-methylbutyloxy group, 3,3,5-trimethylhexyloxy group, 1-isobutyl-3-methylbutyloxy group, cyclohexyloxy group, 2-methylcyclohexyloxy group and 2,4-dimethylcyclohexyloxy group.

Typical examples of the alkyl group represented by $Y^1$, $Y^2$, $Y^3$, $Y^4$, $Y^5$, $Y^6$, $Y^7$ and $Y^8$ include a methyl group, ethyl group, propyl group, n-butyl group, iso-butyl group, tert-butyl group, sec-butyl group, n-pentyl group, isopentyl group, neo-pentyl group, 1-methylbutyl group, 2-methylbutyl group, n-hexyl group, 2-ethylbutyl group, 3-methylpentyl group, 2,3-dimethylbutyl group, n-heptyl group, n-octyl group, 2-ethylhexyl group, n-nonyl group, 2,5,5-trimethylhexyl group, n-decyl group, 4-ethyloctyl group, 4-ethyl-4,5-dimethylhexyl group, n-undecyl group, n-dodecyl group, 1,3,5,7-tetramethyloctyl group, 4-butyl-octyl group, 6,6-diethyloctyl group, n-tridecyl group, 6-methyl-4-butyloctyl group, n-tetradecyl group and n-pentadecyl group.

Typical examples of the alkylthio group include a methylthio group, ethylthio group, n-propylthio group, iso-propylthio group, n-butylthio group, iso-butylthio group, tert-butylthio group, sec-butylthio group, n-pentylthio group, iso-pentylthio group, neo-pentylthio group, 1,2-dimethylpropylthio group, n-hexylthio group, 1-ethyl-2-methylpropylthio group, 2-ethylbutylthio group, cyclohexylthio group, 2-methyl-1-isopropylthio group, n-heptylthio group, 2-methylhexylthio group, 1-ethylpentylthio group, n-octylthio group, 2-ethylhexylthio group, 3-methyl-1-iso-propylbutylthio group, n-nonylthio group, 3-methyl-1-isobutylbutylthio group, 3,5,5-trimethylhexylthio group, and 4-tert-butylcyclohexylthio group.

Examples of the alkyl group represented by $A^1$, $A^2$, $A^3$, $A^4$, $A^5$, $A^6$, $A^7$ and $A^8$ include a methyl group, ethyl group, n-propyl group, iso-propyl group, n-butyl group, iso-butyl group, tert-butyl group, n-pentyl group, iso-pentyl group, neo-pentyl group, n-hexyl group, cyclohexyl group, n-heptyl group, 1,1-diethylpropyl group, n-octyl group, n-nonyl group, n-decyl group, chloromethyl group, hydroxymethyl group, methoxymethyl group and methylthiomethyl group, but particularly preferable examples include the methyl group, ethyl group, iso-propyl group, n-butyl group, iso-butyl group and tert-butyl group.

Examples of the aralkyl group include a benzyl group, tert-butylbenzyl group, phenethyl group, 4-cyclohexylbenzyl group and naphthylmethyl group.

Examples of the alkenyl group include an allyl group, crotyl group and methallyl group, and examples of the alkynyl group include an ethynyl group, propynyl group and phenylethynyl group.

Examples of the alkoxyl group include a methoxy group, ethoxy group, n-propoxy group, iso-propoxy group, n-butoxy group, iso-butoxy group, tert-butoxy group, n-pentoxy group, iso-pentoxy group, neo-pentoxy group, n-hexyloxy group, iso-hexyloxy group, neo-hexyloxy group, cyclohexyloxy group, heptyloxy group, n-octyloxy group, n-nonyloxy group and n-decyloxy group.

Examples of the aryloxy group include a phenoxy group, 4-tert-butylphenyloxy group and naphthyloxy group.

Examples of the alkylthio group include a methylthio group, ethylthio group, n-propylthio group, iso-propylthio group, n-butylthio group, iso-butylthio group, n-pentylthio group, iso-pentylthio group and neo-pentylthio group.

Examples of the arylthio group include a phenylthio group, 4-tert-butylphenylthio group and naphthylthio group.

Each pair of $A^1$ and $A^2$, $A^3$ and $A^4$, $A^5$ and $A^6$, and $A^7$ and $A^8$ may together form a ring and represent the groups:

$$-N=CH-CH=CH-, \quad -O-CH_2CH_2-O-,$$

$$-S-CH_2CH_2-S-, \quad -NH-CH_2CH_2-S-,$$

$$\underset{R}{\overset{|}{-N}}-CH_2CH_2-S-,$$

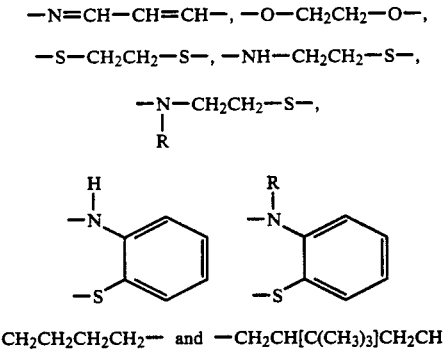

$-CH_2CH_2CH_2CH_2-$ and $-CH_2CH[C(CH_3)_3]CH_2CH_2-$.

Examples of the halogen include fluorine, chlorine, bromine and iodine.

Moreover, examples of divalent metals represented by Met in the formula (I) include $Cu^{(II)}$, $Zn^{(II)}$, $Fe^{(II)}$, $Co^{(II)}$, $Ni^{(II)}$, $Ru^{(II)}$, $Rh^{(II)}$, $Pd^{(II)}$, $Pt^{(II)}$, $Mn^{(II)}$, $Mg^{(II)}$, $Ti^{(II)}$, $Be^{(II)}$, $Ca^{(II)}$, $Ba^{(II)}$, $Cd^{(II)}$, $Hg^{(II)}$, $Pb^{(II)}$ and $Sn^{(II)}$; examples of mono-substituted trivalent metals include Al—Cl, Al—Br, Al—F, Al—I, Ga—Cl, Ga—F, Ga—I, Ga—Br, In—Cl, In—Br, In—I, In—F, Tl—Cl, Tl—Br, Tl—I, Tl—F, Al—$C_6H_5$, Al—$C_6H_4(CH_3)$, In—$C_6H_5$, In—$C_6H_4(CH_3)$, In—$C_{10}H_7$, Mn(OH), Mn($OC_6H_5$), Mn[OSi(CH$_3$)$_3$], FeCl and RuCl. Examples of di-substituted tetravalent metals include CrCl$_2$, SiCl$_2$, SiBr$_2$, SiF$_2$, SiI$_2$, ZrCl$_2$, GeCl$_2$, GeBr$_2$, GeI$_2$, GeF$_2$, SnCl$_2$, SnBr$_2$, SnI$_2$, SnF$_2$, TiCl$_2$, TiBr$_2$, TiF$_2$, Si(OH)$_2$, Ge(OH)$_2$, Zr(OH)$_2$, Mn(OH)$_2$, Sn(OH)$_2$, TiR$_2$, CrR$_2$, SiR$_2$, SnR$_2$, GeR$_2$, wherein R is an alkyl group, phenyl group, naphthyl group or a substituted derivative thereof, Si(OR')$_2$, Sn(OR')$_2$, Ge(OR')$_2$, Ti(OR')$_2$, Cr(OR')$_2$ wherein R' is an alkyl group, phenyl group, naphthyl group, trialkylsilyl group, dialkylalkoxysilyl group or a substituted derivative thereof, Sn(SR'')$_2$ and Ge(SR'')$_2$ wherein R'' is an alkyl group, phenyl group, naphthyl group or a substituted derivative thereof.

Examples of the oxymetal group include VO, MnO and TiO.

The reason why the above-mentioned groups are preferable as the groups for $Y^1$, $Y^2$, $Y^3$, $Y^4$, $Y^5$, $Y^6$, $Y^7$ and $Y^8$ is that they are oriented perpendicular to the surface of each phthalocyanine ring and provide steric hindrance on the ring. Therefore, in the case of the alkyl group, it has 1 or more carbon atoms, preferably 4 or more carbon atoms; in the case of the alkoxyl group, it has 4 or more carbon atoms, preferably it is branched or cyclic; and in the case of the alkylthio group, it has 1 or more carbon atoms. On the other hand, the upper limit of a group size should be selected considering the fact that if the ratio of a chromophoric group in a certain volume is low, the light absorption per unit volume decreases. Thus, with regard to the alkyl group, the upper limit of the carbon atom number is 15, preferably 10; and with regard to the alkoxyl group, the upper limit of the carbon atom number is 15, preferably 9.

Furthermore, $A^1$, $A^2$, $A^3$, $A^4$, $A^5$, $A^6$, $A^7$ and $A^8$ are groups for assisting $Y^1$, $Y^2$, $Y^3$, $Y^4$, $Y^5$, $Y^6$, $Y^7$ and $Y^8$ in extending perpendicularly from the phthalocyanine ring. Likewise, the size of $A^1$, $A^2$, $A^3$, $A^4$, $A^5$, $A^6$, $A^7$ and $A^8$ should be selected so as not to decrease the light absorption per unit volume. Preferably, the alkyl group, aralkyl group, alkenyl group, alkynyl group, alkoxyl group or alkylthio group has 1 to 4 carbon atoms when it is straight-chain, and it has 4 to 6 carbon atoms when it is branched or cyclic. The aryloxy group, for example, the phenyloxy group, naphthyloxy group or 4-tert-butylphenoxy group preferably has 6 to 10 carbon atoms. Moreover, the arylthio group, for example, the phenylthio group, 4-tert-butylphenylthio group, naphthylthio group or 2-methylphenylthio group preferably has 6 to 10 carbon atoms.

The near infrared absorber of the present invention is characterized in that the alkoxyl group having 4 to 15 carbon atoms, preferably 4 to 9 carbon atoms, is introduced into the α-position of the phthalocyanine, i.e., $Y^1$, $Y^2$, $Y^3$, $Y^4$, $Y^5$, $Y^6$, $Y^7$ and $Y^8$ in order to successfully inhibit the association of the phthalocyanine by the steric hindrance resulting from the introduced group.

The compound represented by the formula (I) can be synthesized by mixing one to four kinds of compounds having the formula (II) or (III)

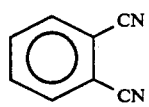

(II)

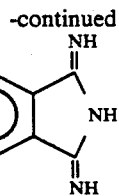

(III)

in which the benzene ring may have such substituents as are mentioned in the paragraphs regarding the formula (I), and then thermally reacting the mixture with a metallic derivative in the presence of, e.g., 1,8-diazabicyclo[5.4.0]-7-undecene (DBU) in an alcohol, or alternatively reacting the mixture with a metallic derivative in a high-boiling solvent such as chloronaphthalene, bromonaphthalene or trichlorobenzene.

The manufacture of optical recording media by the use of the near infrared absorbers of the present invention can be achieved by a method comprising the step of applying or depositing the near infrared absorber on transparent substrates. In the applying method, a binder resin and the near infrared absorber are dissolved in a solvent so that the concentration of the binder resin and the near infrared absorbers may be 20% by weight or less, preferably 0%, i.e., absent and 0.05 to 20% by weight, preferably 0.5 to 20% by weight, respectively, and then application is carried out by using a spin coater. Furthermore, in the above-mentioned depositing method, the near infrared absorber is deposited on substrates under $10^{-5}$ to $10^{-7}$ Torr at 100° to 300° C.

However, for the purpose of exerting the performance of the near infrared absorber of the present invention which is superior to that of conventional absorbers, the application method of using the spin coater and a dipping method are preferable, and in particular, a method of applying the near infrared absorber of the present invention alone is best. The optical recording media may be WORM type or CD-WORM type. The WORM type recording medium can be manufactured only by disposing a recording layer comprising the near infrared absorber of the present invention on the substrate, and the CD-WORM type recording medium can be manufactured by disposing the recording layer on the substrate, then superposing thereon a reflective layer comprising gold or aluminum, and finally overcoating the layer with a resin.

The substrates can be made from optically transparent resins. Examples of such resins include acrylic resin, polyethylene resin, vinyl chloride resin, vinylidene chloride resin, polycarbonate resin, ethylene resin, polyolefin copolymer resin, vinyl chloride copolymer resin, vinylidene chloride copolymer resin and styrene copolymer resin.

Furthermore, the substrates may be surface-treated with a thermosetting resin or an ultraviolet-setting resin. In particular, the latter treated one is called 2P substrate.

When optical recording media (optical discs and optical cards) are manufactured, it is preferred from the viewpoints of cost and users' handling that the polyacrylate or polycarbonate substrates are employed and that the application is made by the spin coating technique.

Considering solvent resistance of the substrates, such a solvent as exemplified below is preferably used in the spin coating. Examples of such preferably usable solvents include hydrocarbon halides (e.g., dichloromethane, chloroform, carbon tetrachloride, tetrachloroethylene, dichlorodifluoroethane), ethers (e.g., tetrahydrofuran and diethyl ether), ketones (e.g., acetone and methyl ethyl ketone), alcohols (e.g., methanol, ethanol and propanol), CELLOSOLVE®s (methyl CELLOSOLVE®2-methoxyethanol and ethyl CELLOSOLVE® 2-ethoxyethanol), and hydrocarbons (hexane, cyclohexane, octane, benzene, toluene and xylene).

In the manufacture of the filters, the near infrared absorber compound represented by the formula (I) should have a heat resistance which permits the compound to be kneaded with the resin, and it is also required that the resin substrates can be dyed in the solvent, from the viewpoints of cost and workability. In addition, the molded articles, i.e., manufactured filters should possess sharp light absorption properties and high absorbance.

As techniques of preparing the near infrared absorption filters by using the compound having the formula (I) or its derivative, there are (a) a method comprising the steps of mixing the near infrared absorber of the formula (I) with a resin, and then molding the mixture; (b) a method comprising the steps of mixing the near infrared absorber of the formula (I) with a resin monomer, and then cast-polymerizing the mixture; (c) a method comprising the step of dyeing molded resin articles with the near infrared absorber of the formula (I); and (d) a method comprising the step of applying or depositing the near infrared absorber of the formula (I) on the surface of the substrate materials.

The resins which can be used as filter base materials are preferably transparent. Examples of such preferable resins include thermoplastic resins such as a polystyrene, polymethyl methacrylate, polycarbonate, polyethylene and polypropylene; and thermosetting resins such as CR-39 (trade name; made by PPG Co., Ltd.), MR-3 (trade name; made by Mitsui Toatsu Chemicals, Inc.) and MR-6 (trade name; made by Mitsui Toatsu Chemicals, Inc.).

Furthermore, when the near infrared absorber of the present invention is used as a display material together with liquid crystals, the absorber must be highly soluble in the liquid crystals, and when the state of the liquid crystals is changed by applying an electric field or heat thereto, it is necessary that the absorber does not impede this change of the liquid crystals.

In the case when display materials are prepared, examples of the usable liquid crystals include nematic liquid crystals, smectic liquid crystals and cholesteric liquid crystals. As display techniques, suitable examples include a guest/host type display system and a liquid crystal panel system (the near infrared absorber is added to the liquid crystals, and an image is then written by the use of a laser beam).

Having generally described this invention, a further understanding can be obtained by reference to certain specific examples which are provided herein for purposes of illustration only and are not intended to be limiting unless otherwise specified.

EXAMPLES

Example 1

A mixture of 906 parts of a phthalonitrile derivative represented by the following structural formula (II-1), 79 parts of cuprous chloride, 608 parts of 1,8-diazabicyclo[5.4.0]-7-undecene (DBU) and 7,500 parts of n-amyl alcohol was heated under reflux for 5 hours:

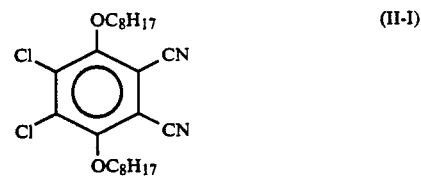

Methyl alcohol was then added to the resulting reaction solution in order to precipitate crystals, and the latter were collected by suction filtration and then purified through a column (silica gel/toluene), so that 600 parts (yield 60%) of a phthalocyanine compound represented by the following structural formula (I-1) was obtained ($\lambda$max 738 nm/hexane; $\epsilon$max 227,000):

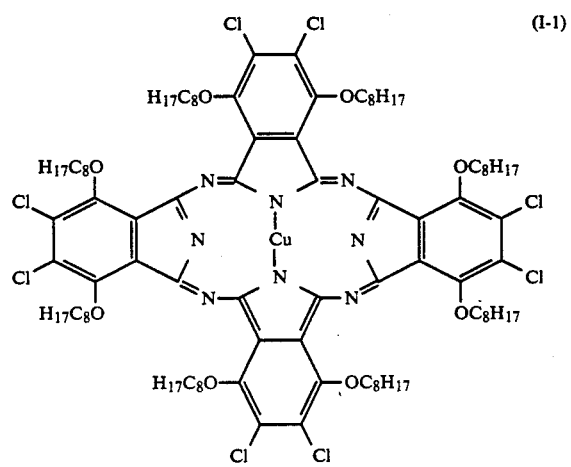

Results of elemental analysis (as Cu $C_{96}H_{136}N_8O_8Cl_8$):

| | C | H | N | Cl |
|---|---|---|---|---|
| Calcd. (%) | 61.42 | 7.30 | 5.97 | 15.11 |
| Found (%) | 61.20 | 7.27 | 5.93 | 15.09 |

In 100 parts of n-octane was dissolved 1 part of the obtained compound (I-1), and the solution was then applied onto a polycarbonate optical disc substrate. The thus-obtained optical disc had a reflectance of 29% and a sensitivity of 50 dB at 8 mW, 780 nm and a linear velocity of 5.5 m/sec.

Furthermore, 7 parts of the above compound (I-1) was mixed with 1,000 parts of a cyanobiphenyl liquid crystal mixture in order to prepare a liquid crystal panel. When an image was depicted on this panel by the use of a laser beam, it appeared distinctly thereon.

Example 2

A mixture of 320 parts of a phthalonitrile derivative represented by the structural formula (II-1), 75 parts of acetylacetone vanadium, 214 parts of DBU and 2,700 parts of n-amyl alcohol was heated under reflux for 10 hours. After the solvent was distilled off, the residue was purified through a column (toluene), so that 37 parts (yield 11%) of a phthalocyanine compound represented by the following structural formula (I-2) was obtained ($\lambda$max 762 nm/hexane; $\epsilon$max 220,000):

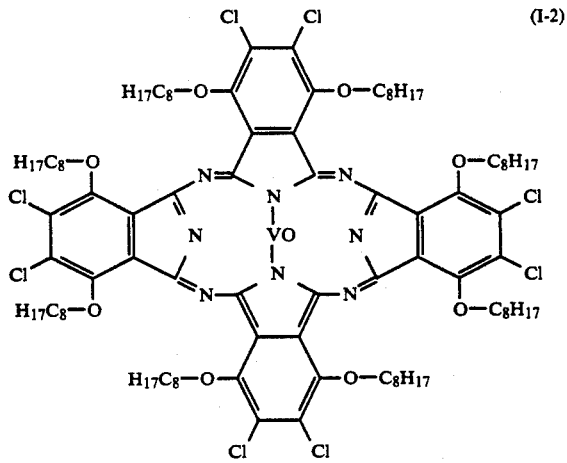

(I-2)

Results of elemental analysis (as V $C_{96}H_{136}N_8O_9Cl_8$):

|  | C | H | N | Cl |
|---|---|---|---|---|
| Calcd. (%) | 61.31 | 7.29 | 5.96 | 15.08 |
| Found (%) | 61.27 | 7.25 | 5.90 | 15.06 |

In 1,000 parts of n-octane was dissolved 15 parts of the phthalocyanine represented by the formula (I-2), and the resulting solution was then applied onto a polycarbonate optical disc substrate. The thus-obtained optical disc had a reflectance of 27% and a sensitivity (C/N ratio) of 50 dB at 8 mW, 780 nm and a linear velocity of 5.5 m/sec.

Furthermore, 1 part of the above compound (I-2) was dissolved in 100 parts of a liquid crystal mixture having the following formulae in order to prepare a liquid crystal panel.

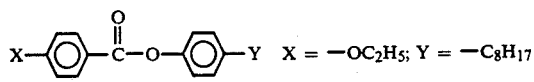

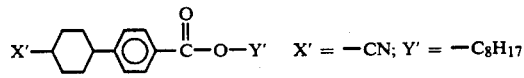

When an image was depicted on this panel by the use of a laser beam, it appeared distinctly thereon.

Example 3

A mixture of 368 parts of a phthalonitrile derivative represented by the following structural formula (II-2), 44 parts of 90% cuprous chloride, 304 parts of DBU and 3,100 parts of n-amyl alcohol was heated under reflux for 5.5 hours:

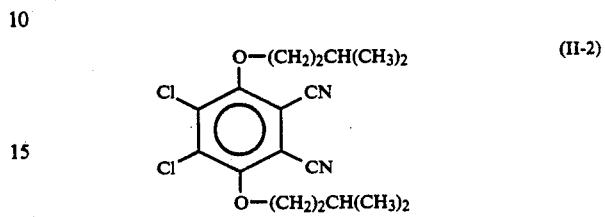

(II-2)

Afterward, the resulting reaction solution was poured into 3,200 parts of methyl alcohol, and the product was isolated by suction filtration. The thus-obtained crystals were purified through a column (silica gel/hexane toluene=1:1), so that 220 parts (yield 57%) of a phthalocyanine compound represented by the following structural formula (I-3) was obtained ($\lambda$max 778 nm/hexane; $\epsilon$max 234,000):

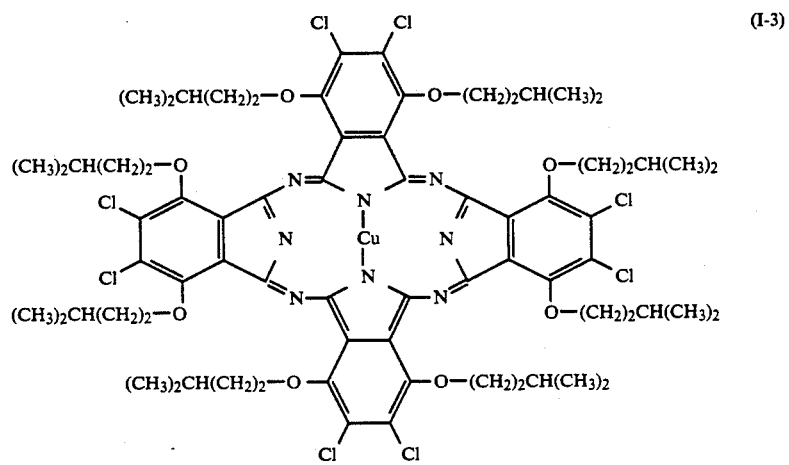

(I-3)

Results of elemental analysis (as Cu $C_{72}H_{88}N_8O_8Cl_8$):

|  | C | H | N | Cl |
|---|---|---|---|---|
| Calcd. (%) | 56.13 | 5.76 | 7.27 | 18.41 |
| Found (%) | 56.02 | 5.80 | 7.24 | 18.34 |

In 100 parts of dibutyl ether was dissolved 1 part of the above-mentioned compound (I-3), and the resulting solution was then applied onto a polycarbonate optical disc substrate. The thus-obtained optical disc had a reflectance of 39% and a sensitivity of 51 dB at 8 mW, 780 nm and a linear velocity of 5.5 m/sec.

Furthermore, 7 parts of the above compound (I-3) was dissolved in 1,000 parts of a cyanobiphenyl liquid crystal mixture in order to prepare a liquid crystal panel. When an image was depicted on this panel by the use of a laser beam, it appeared distinctly thereon.

In 100 parts of n-octane was dissolved 1 part of the above-mentioned compound (I-3), and the resulting solution was then applied onto a polycarbonate optical card substrate. Afterward, the applied substrate was further coated with a resin to prepare an optical card. The thus-obtained optical card had a reflectance of 39% and a sensitivity of 50 dB at 8 mW, 780 nm and a linear velocity of 2.8 m/sec. Durability of this card was good.

Four parts of the above-mentioned compound (I-3) was mixed with 1,000 parts of polystyrene resin with heating, and then molded into the shape of a plate. The thus-prepared filter sufficiently absorbed rays at 750 to 850 nm.

COMPARATIVE EXAMPLES 1 to 3

In each comparative example, the following known compound was used.

In Table 1, the results of the above examples are compared with those of the comparative examples in regard to maximum absorption wavelength ($\lambda$max) in a solution state of each compound, molecular extinction coefficient ($\epsilon$) at its wavelength, solubility, maximum reflectance and sensitivity.

In Comparative Example 1:

Exemplary Compound 4 of Japanese Patent Laid-open Publication No. 152,769/1986:

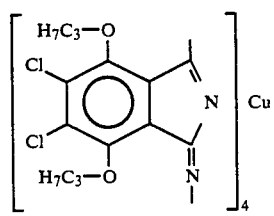

Since it is insoluble in n-octane, this compound was dissolved in chloroform, and the resulting solution was then applied onto a 2P substrate. Afterward, the thus-obtained medium was evaluated.

In Comparative Example 2:

The compound in Example 1 of Japanese Patent Laid-open Publication No. 209,583/1985:

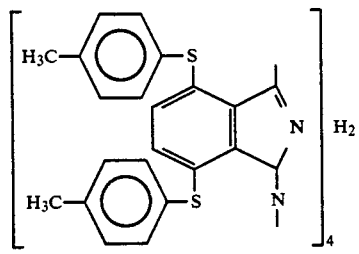

Since it is insoluble in n-octane, this compound was dissolved in chloroform, and the resulting solution was then applied onto a 2P substrate. Afterward, the thus-obtained medium was evaluated.

In Comparative Example 3:

Exemplary Compound 10 in Japanese Patent Laid-open Publication No. 197,280/1986: Deca($-OC_5H_{11}$)$-H_2Pc$ The carbon tetrachloride solution of this compound was applied onto a 2P substrate, and the thus-obtained medium was evaluated.

The items to be measured, measurement procedures and expressions of measured results were as follows:

1. Maximum absorption wavelength ($\lambda$max) and molecular extinction coefficient ($\epsilon$) at that wavelength:

Each of these items was measured at a concentration of 5 mg/l in n-hexane or chloroform.

2. Solubility:

Solubility was ranked as follows:

O: when dissolved 5 g/l or more in n-hexane, $\Delta$: when dissolved less than 5 g/l in n-hexane, and when dissolved 5 g/l or more in carbon tetrachloride, and X: when dissolved less than 5 g/l in carbon tetrachloride.

3. Maximum reflectance:

Maximum reflectance was measured by applying a 5 g/l n-hexane solution onto each polycarbonate substrate by the use of a spin coater, and then irradiating the applied substrate with rays at 780 nm.

4. Sensitivity:

Sensitivity was obtained from a C/N ratio when writing was carried out with a semiconductor laser at 780 nm, 8 mW and a linear velocity of 5.5 m/sec.

O: 40 dB or more, $\Delta$: 40 to 30 dB, and

X: less than 30 dB.

TABLE 1

| | $\lambda$max ($\epsilon$) | Solubility | Maximum Reflectance | Sensitivity |
|---|---|---|---|---|
| Example 1 | 738 (2.27 × 10$^5$) | O | 30 | O |
| Example 2 | 762 (2.2 × 10$^5$) | O | 30 | O |
| Example 3 | 738 (2.34 × 10$^5$) | O | 42 | O |
| Comp. Ex. 1 | 740 (1.5 × 10$^5$) | X | 24 | $\Delta$ |
| Comp. Ex. 2 | 780 (1.5 × 10$^5$) | X | 27 | $\Delta$ |
| Comp. Ex. 3 | 760 (1.5 × 10$^5$) | $\Delta$ | 20 | X |

EXAMPLE 4

A mixture of 4.11 parts of a phthalonitrile derivative represented by the following structural formula (II-3), 0.44 part of cuprous chloride, 3.04 parts of DBU and 37.5 parts of n-amyl alcohol was heated under reflux for 5 hours:

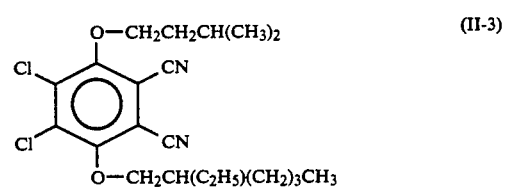

The resulting reaction solution was poured into 400 parts of methyl alcohol in order to precipitate crystals, and the latter were collected by suction filtration and then purified through a column (silica gel/hexane:-toluene=5:2), so that 2.50 parts (yield 59%) of a phthalocyanine compound represented by the following structural formula (I-4) and its isomers were obtained ($\lambda$max 742 nm/hexane; $\epsilon$max 2.3×10$^5$):

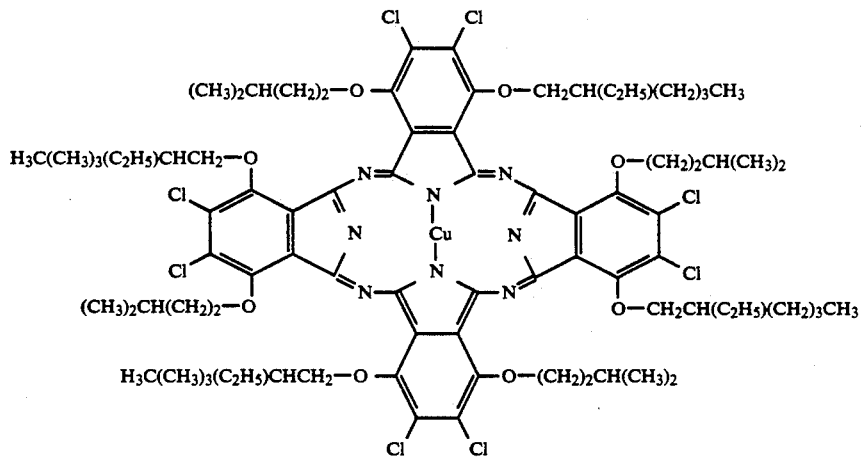

(I-4)

Results of elemental analysis (as Cu $C_{84}H_{112}N_8Cl_8O_8$):

|  | C | H | N | Cl |
|---|---|---|---|---|
| Calcd. (%) | 59.03 | 6.61 | 6.56 | 16.60 |
| Found (%) | 58.98 | 6.63 | 6.54 | 16.55 |

Next, 5 parts of the obtained phthalocyanine derivative (I-4) was mixed with 1,000 parts of polystyrene resin with heating and then molded into the shape of a plate. The thus-obtained filter sufficiently absorbed rays at 750 to 850 nm.

Furthermore, 1 part of the phthalocyanine (I-4) was dissolved in 100 parts of a liquid crystal mixture having the following formula, and a liquid crystal panel was then prepared by using the solution:

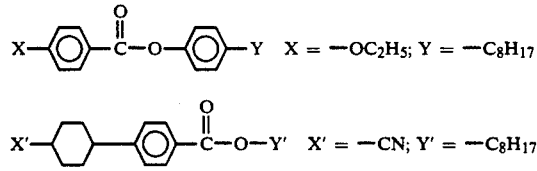

When an image was written on this panel by the use of a laser beam, it appeared distinctly thereon.

Example 5

A mixture of 4.26 parts of a phthalonitrile derivative represented by the following structural formula (II-4), 0.53 part of cuprous chloride, 3.65 parts of DBU and 45.0 parts of n-amyl alcohol was heated under reflux for 6 hours:

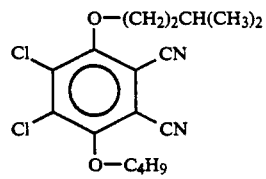

(II-4)

The resulting reaction mixture was poured into 500 parts of methyl alcohol in order to precipitate crystals, and the latter were collected by suction filtration and then purified through a column (silica gel/hexane:-toluene=5:3), so that 2.50 parts (yield 56%) of a phthalocyanine compound represented by the following structural formula (I-5) was obtained ($\lambda$max 739 nm/hexane; $\epsilon$max $2.5 \times 10^5$):

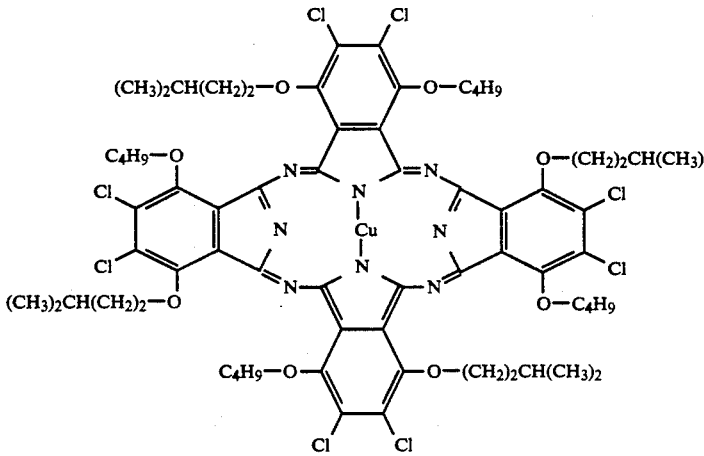

(I-5)

Results of elemental analysis (as Cu $C_{68}H_{80}N_8Cl_8O_8$):

|  | C | H | N | Cl |
|---|---|---|---|---|
| Calcd. (%) | 55.01 | 5.43 | 7.55 | 19.10 |
| Found (%) | 54.98 | 5.44 | 7.53 | 19.07 |

Next, 4 parts of the obtained phthalocyanine derivative (I-5) was mixed with 1,000 parts of polystyrene resin with heating and then molded into the shape of a plate. The thus-obtained filter sufficiently absorbed rays at 750 to 850 nm.

Furthermore, 7 parts of the phthalocyanine (I-5) was dissolved in 1,000 parts of a cyanobiphenyl liquid crystal mixture, and a liquid crystal panel was then prepared by using the solution. When an image was written on this panel by the use of a laser beam, it appeared distinctly thereon:

Example 6

A mixture of 4.43 parts of a phthalonitrile derivative represented by the following structural formula (II-5), 0.53 part of cuprous chloride, 3.65 parts of DBU and 45.0 parts of n-amyl alcohol was heated under reflux for 6 hours:

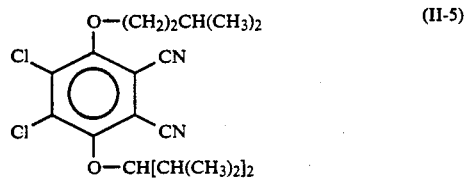

The resulting reaction mixture was poured into 500 parts of methyl alcohol in order to precipitate crystals, and the latter were collected by suction filtration and then purified through a column (silica gel/hexane:toluene=5:2), so that 2.45 parts (yield 53%) of a phthalocyanine compound represented by the following structural formula (I-6) and its isomers were obtained ($\lambda$max 739 nm/hexane; $\epsilon$max $2.42\times 10^5$):

Results of elemental analysis (as Cu $C_{80}H_{104}N_8Cl_8O_8$):

|  | C | H | N | Cl |
|---|---|---|---|---|
| Calcd. (%) | 58.13 | 6.34 | 6.78 | 17.16 |
| Found (%) | 58.90 | 6.26 | 6.83 | 17.30 |

Next, 5 parts of the obtained phthalocyanine derivative (I-6) was mixed with 1,000 parts of polystyrene resin with heating and then molded into the shape of a plate. The thus-obtained filter sufficiently absorbed rays at 750 to 850 nm.

Furthermore, 8 parts of the phthalocyanine (I-6) was dissolved in 1,000 parts of a cyanobiphenyl liquid crystal mixture, and a liquid crystal panel was then prepared by using the solution. When an image was written on this panel by the use of a laser beam, it appeared distinctly thereon:

Example 7

A mixture of 4.06 parts of a phthalonitrile derivative represented by the following structural formula (II-6), 0.53 part of cuprous chloride, 3.65 parts of DBU and 45.0 parts of n-amyl alcohol was heated at reflux for 7 hours:

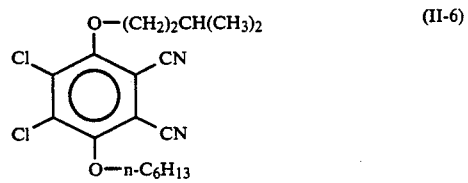

The resulting reaction mixture was poured into 500 parts of methyl alcohol in order to precipitate crystals, and the latter were collected by suction filtration and then purified through a column (silica gel/hexane:toluene=5:2), so that 2.63 parts (yield 55%) of a phthalocyanine compound represented by the following structural formula (I-7) and its isomers were obtained ($\lambda$max 739 nm/hexane; $\epsilon$max $2.4\times 10^5$):

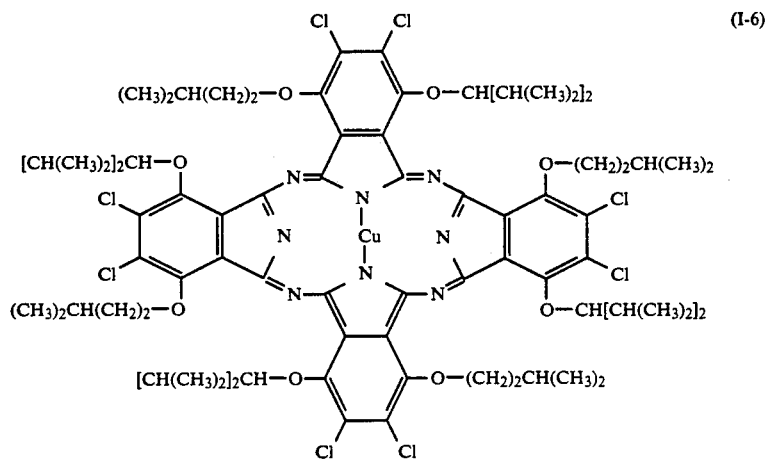

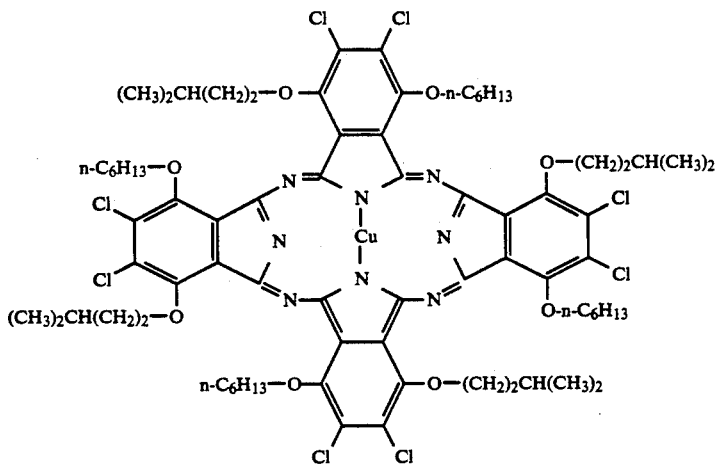

(I-7)

Results of elemental analysis (as Cu $C_{76}H_{96}N_8Cl_8O_8$):

|  | C | H | N | Cl |
|---|---|---|---|---|
| Calcd. (%) | 57.17 | 6.06 | 7.02 | 17.76 |
| Found (%) | 57.15 | 6.09 | 7.00 | 17.73 |

Next, 5 parts of the obtained phthalocyanine derivative (I-7) was mixed with 1,000 parts of polystyrene resin with heating and then molded into the shape of a plate. The thus-obtained filter sufficiently absorbed rays at 750 to 850 nm.

Furthermore, 8 parts of the phthalocyanine (I-7) was dissolved in 1,000 parts of a cyanobiphenyl liquid crystal mixture, and a liquid crystal panel was then prepared by using the solution. When an image was written on this panel by the use of a laser beam, it appeared distinctly thereon:

Example 8

A mixture of 4.26 parts of a phthalonitrile derivative represented by the following structural formula (II-7), 0.53 part of cuprous chloride, 3.65 parts of DBU and 45.0 parts of n-amyl alcohol was heated at reflux for 7 hours:

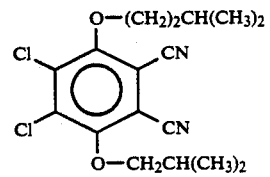

(II-7)

The resulting reaction mixture was poured into 500 parts of methyl alcohol in order to precipitate crystals, and the latter were collected by suction filtration and then purified through a column (silica gel/hexane:toluene=5:2), so that 2.10 parts (yield 57%) of a phthalocyanine compound represented by the following structural formula (I-8) and its isomers were obtained (λmax 742 nm/hexane; εmax $2.23 \times 10^5$):

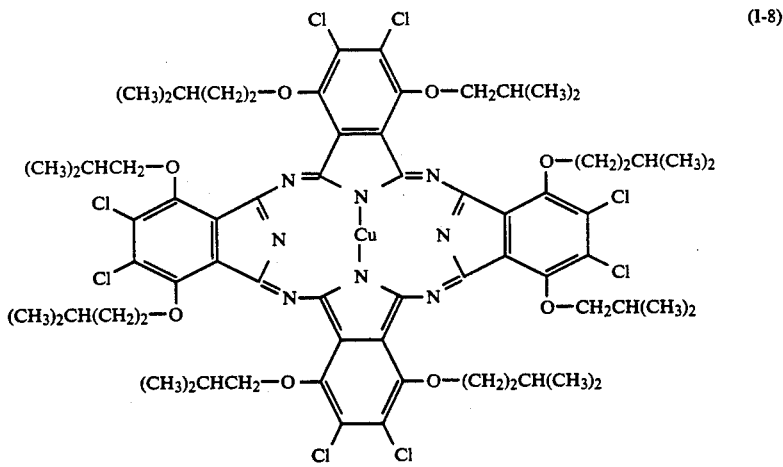

(I-8)

Results of elemental analysis (as Cu $C_{68}H_{80}N_8Cl_8O_8$):

|  | C | H | N | Cl |
|---|---|---|---|---|
| Calcd. (%) | 55.01 | 5.43 | 7.55 | 19.10 |
| Found (%) | 54.97 | 5.45 | 7.52 | 19.08 |

Next, 4 parts of the obtained phthalocyanine derivative (I-8) was mixed with 1,000 parts of polystyrene resin with heating and then molded into the shape of a plate. The thus-obtained filter sufficiently absorbed rays at 750 to 850 nm.

Furthermore, 7 parts of the phthalocyanine (I-8) was dissolved in 1,000 parts of a cyanobiphenyl liquid crystal mixture, and a liquid crystal panel was then prepared by using the solution. When an image was written on this panel by the use of a laser beam, it appeared distinctly thereon.

Moreover, 1 part of the phthalocyanine derivative (I-8) was dissolved in 100 parts of dibutyl ether, and the resulting solution was then applied onto a polycarbonate optical card substrate. Afterward, the resulting recording layer was coated with a resin in order to prepare an optical card. The thus-prepared card had a reflectance of 35% and a sensitivity (C/N ratio) of 50 dB at 780 nm, 8 mW and a linear velocity of 2.8 m/sec. In addition, the durability of the card was also good.

Example 9

A mixture of 43 parts of $SiCl_4$ and 3,000 parts of quinoline was heated up to 200° C. To this mixture was added 386 parts of the diiminoisoindoline derivative represented by the following structural formula (III-1), and the solution was then heated at reflux for 5 hours:

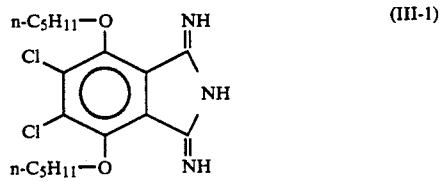

(III-1)

The resulting reaction solution was poured into 3,500 parts of methyl alcohol in order to precipitate crystals, and the latter were collected by suction filtration and then washed with methanol, followed by drying, thereby obtaining 157 parts (yield 40%) of a phthalocyanine compound represented by the following structural formula (I-9) ($\lambda$max 740 nm/hexane; $\epsilon$max $2.4 \times 10^5$):

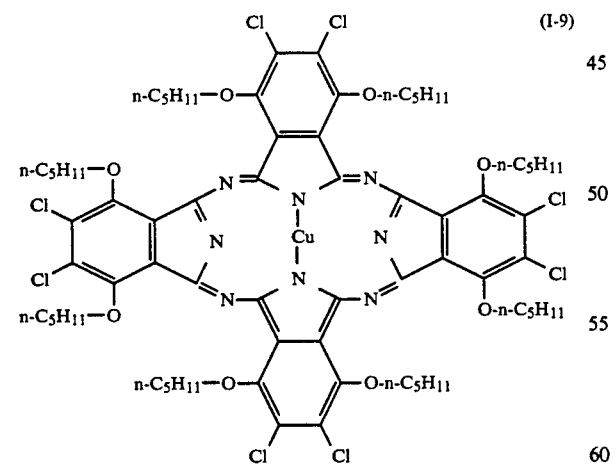

(I-9)

Results of elemental analysis (as Si $C_{72}H_{88}N_8O_8Cl_{10}$):

|  | C | H | N | Cl |
|---|---|---|---|---|
| Calcd. (%) | 54.87 | 5.63 | 7.11 | 22.49 |
| Found (%) | 54.69 | 5.59 | 7.09 | 22.36 |

Next, 1 part of the obtained compound (I-9) was dissolved in 100 parts of dibutyl ether, and the resulting solution was applied onto a polycarbonate optical disc substrate. The thus-obtained optical disc had a reflectance of 36% and a sensitivity (C/N ratio) of 51 dB at 780 nm, 8 mW and a linear velocity of 5.5 m/sec.

Furthermore, 7 parts of the phthalocyanine (I-9) was dissolved in 1,000 parts of a cyanobiphenyl liquid crystal mixture, and a liquid crystal panel was then prepared by using the solution. When an image was written on this panel by the use of a laser beam, it appeared distinctly thereon.

Moreover, 1 part of the compound (I-9) was dissolved in 100 parts of dibutyl ether, and the resulting solution was then applied onto a polycarbonate optical card substrate. Afterward, the resulting recording layer was coated with a resin in order to prepare an optical card. The thus-prepared card had a reflectance of 36% and a sensitivity (C/N ratio) of 51 dB at 780 nm, 8 mW and a linear velocity of 2.8 m/sec.

Next, 4 parts of the obtained compound (I-9) was mixed with 1,000 parts of polystyrene resin with heating and then molded into the shape of a plate. The thus-obtained filter sufficiently absorbed rays at 750 to 850 nm.

Examples 10 to 44

Phthalocyanines shown in Table 4 were synthesized by reacting 1 to 4 kinds of phthalonitriles (Table 2) represented by the following formula (II) or diiminoisoindolines (Table 3) represented by the following formula (III) with metal derivatives. The synthesized compounds had great molecular extinction coefficients, and when optical recording media were prepared from these compounds, they were also excellent in reflectance, sensitivity and durability. The results are given in Table 4.

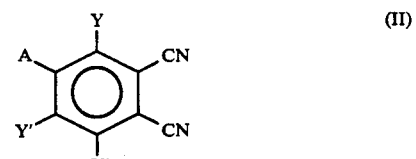

(II)

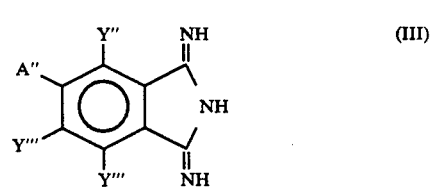

(III)

TABLE 2

| Intermediate | Y | Y' | A | A' |
|---|---|---|---|---|
| II-8 | iso-$C_5H_{11}$—O | n-$C_4H_9$—O | $C_6H_5S$— | $C_6H_5S$— |
| II-9 | iso-$C_5H_{11}$—O | n-$C_5H_{11}$—O | $C_6H_5S$— | $C_6H_5S$— |
| II-10 | iso-$C_5H_{11}$—O | n-$C_6H_{13}$—O | $C_6H_5S$— | $C_6H_5S$— |

TABLE 2-continued

| Intermediate | Y | Y' | A | A' |
|---|---|---|---|---|
| II-11 | iso-$C_5H_{11}$—O | iso-$C_4H_9$—O | $C_6H_5S$— | $C_6H_5S$— |
| II-12 | iso-$C_5H_{11}$—O | $CH_3(CH_2)_3CH(C_2H_5)CH_2$—O | $C_6H_5S$— | $C_6H_5S$— |
| II-13 | iso-$C_5H_{11}$—O | n-$C_5H_{11}$—O |  |  |
| II-14 | iso-$C_5H_{11}$—O | iso-$C_4H_9$—O |  |  |
| II-15 | iso-$C_5H_{11}$—O | iso-$C_4H_9$—O | 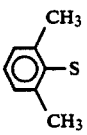 | 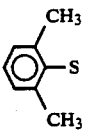 |
| II-16 | iso-$C_5H_{11}$—O | $CH_3(CH_2)_3CH(C_2H_5)CH_2$—O | $C_{10}H_7S$— | $C_{10}H_7S$— |
| II-17 | n-$C_8H_{17}$—O | $CH_3(CH_2)_3CH(C_2H_5)CH_2$—O | $C_{10}H_7S$— | $C_{10}H_7S$— |
| II-18 | iso-$C_5H_{11}$—O | $(CH_3)_3CCH_2CH(CH_3)(CH_2)_2$—O | $CH_3$— | $CH_3$— |
| II-19 | $CH_3(CH_2)_3CH(C_2H_5)CH_2$—O | $(CH_3)_3CCH_2CH(CH_3)(CH_2)_2$—O | $C_2H_5$— | $C_2H_5$— |
| II-20 | n-$C_{12}H_{25}$—O | n-$C_{16}H_{33}$—O | $CH_3S$— | $CH_3S$— |
| II-21 | n-$C_6H_{13}$—O | cyclo-$C_6H_{11}$—O | $CH_3S$— | $CH_3S$— |
| II-22 | iso-$C_5H_{11}$—O | iso-$C_4H_9$—O | n-$C_4H_9S$— | n-$C_4H_9S$— |
| II-23 | $C_2H_5OC_2H_4$—O | n-$C_8H_{17}O$ | $CH_3$— | $CH_3$— |
| II-24 | $C_2H_5OC_2H_4OC_2H_4$—O | $[(CH_3)_2CHCH_2]_2CHO$— | $CH_3$— | $CH_3$— |
| II-25 | $HOCH_2CH_2$—O | $CH_3(CH_2)_3CH(C_2H_5)CH_2$—O | $CH_3$— | $CH_3$— |
| II-26 | iso-$C_5H_{11}$—O | iso-$C_4H_9$—O | $C_3H_6$— | $C_3H_6$— |
| II-27 | $(CH_3)_2NC_2H_4$—O | $CH_3(CH_2)_3CH(C_2H_5)CH_2$—O | $C_6H_5S$— | $C_6H_5S$— |
| II-28 | $C_2H_5SC_2H_4$—O | $CH_3(CH_2)_3CH(C_2H_5)CH_2$—O | $C_6H_5S$— | $C_6H_5S$— |
| II-29 | 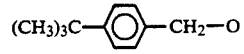 | $CH_3(CH_2)_3CH(C_2H_5)CH_2$—O | cyclo-$C_6H_{11}S$— | cyclo-$C_6H_{11}S$— |
| II-30 | $(CH_3)_3C=CHCH_2$—O | iso-$C_5H_{11}$—O | $CH_3$— | $CH_3$— |
| II-31 | $C_2H_5OC_2H_4$—O | $(CH_3)_2NC_2H_4$—O | $CH_3$— | $CH_3$— |
| II-32 | $C_2H_5OC_2H_4$—O | $C_2H_5SC_2H_4$—O | $C_6H_5S$— | $C_6H_5S$— |

TABLE 3

| Intermediate | Y'' | Y''' | A'' | A''' |
|---|---|---|---|---|
| III-2 | iso-$C_5H_{11}$—O | iso-$C_4H_9$—O | $CH_3$ | $CH_3$ |
| III-3 | iso-$C_5H_{11}$—O | $CH_3(CH_2)_3CH(C_2H_5)CH_2$—O | $C_6H_5O$— | $C_6H_5O$— |
| III-4 | $CH_3$— | $[(CH_3)_2CHCH_2]_2CH$—O | Cl— | Cl— |
| III-5 | $C_2H_5OC_2H_4$—O | n-$C_8H_{17}$—O | Cl— | Cl— |
| III-6 | $C_2H_5SC_2H_4$—O | $CH_3(CH_2)_3CH(C_2H_5)CH_2$—O | $C_6H_5S$— | $C_6H_5S$— |

TABLE 4

| Compound | Central Metal | Manufacturing Process | λmax |
|---|---|---|---|
| I-10 | Cu | Reaction of CuCl, intermediate (II-8) and DBU in amyl alcohol | 778 |
| I-11 | VO | Reaction of VO(acac)$_2$, intermediate (II-9) and DBU in amyl alcohol | 809 |
| I-12 | Ni | Reaction of NiCl$_2$, intermediate (II-10) and DBU in amyl alcohol | 780 |
| I-13 | Cu | Reaction of CuCl, intermediate (II-11) and DBU in amyl alcohol. | 781 |
| I-14 | Pd | Reaction of PdCl$_2$, intermediate (II-12) and DBU in amyl alcohol | 781 |
| I-15 | VO | Reaction of VO(acac)$_2$, intermediate (II-13) and DBU in amyl alcohol | 809 |
| I-16 | Fe | Reaction of FeCl$_2$, intermediate (II-14) and DBU in amyl alcohol | 775 |
| I-17 | Cu | Reaction of CuCl, intermediate (II-15) and DBU in amyl alcohol | 781 |
| I-18 | VO | Reaction of VO(acac)$_2$, intermediate (II-16) and DBU in amyl alcohol | 816 |
| I-19 | Cu | Reaction of CuCl, intermediate (II-17) and DBU in amyl alcohol | 788 |
| I-20 | Pb | Reaction of Pb(OAc)$_2$, intermediate (II-18) and DBU in amyl alcohol | 780 |
| I-21 | VO | Reaction of VCl$_3$ and intermediate (II-19) in chloronaphthalene | 763 |
| I-22 | Cu | Reaction of CuCl, intermediate (II-20) and DBU in amyl alcohol | 739 |
| I-23 | Ni | Reaction of NiCl$_2$, intermediate (II-21) and DBU in amyl alcohol | 746 |
| I-24 | Co | Reaction of CoCl$_2$, intermediate (II-22) and DBU in amyl alcohol | 770 |
| I-25 | Pt | Reaction of PtCl$_2$, intermediate (II-23) and DBU in amyl alcohol | 745 |
| I-26 | VO | Reaction of VO(acac)$_2$, intermediate (II-24) and DBU in amyl alcohol | 767 |
| I-27 | Cu | Reaction of CuCl, intermediate (II-25) and DBU in amyl alcohol | 754 |
| I-28 | VO | Reaction of VCl$_3$, intermediate (II-26) and DBU in chloronaphthalene | 772 |
| I-29 | Cu | Reaction of CuCl, intermediate (II-27) and DBU in amyl alchol | 745 |
| I-30 | VO | Reaction of VO(acac)$_2$, intermediate (II-28) and DBU in amyl alcohol | 812 |
| I-31 | Cu | Reaction of CuCl, intermediate (II-29) and DBU in amyl alcohol | 750 |
| I-32 | Cu | Reaction of CuCl, intermediate (II-30) and DBU in amyl alcohol | 745 |
| I-33 | Cu | Reaction of CuCl, intermediate | 750 |

TABLE 4-continued

| Compound | Central Metal | Manufacturing Process | λmax |
|---|---|---|---|
| I-34 | VO | (II-31) and DBU in amyl alcohol Reaction of VCl₃, intermediate (II-32) and DBU in chloronaphthalene | 820 |
| I-35 | Zn | Reaction of Zn(OAc)₂, intermediate (II-1) and DBU in amyl alcohol | 745 |
| I-36 | Mn(OH)₂ | Reaction of MnCl₂, intermediate (II-2) and DBU in amyl alcohol | 790 |
| I-37 | InCl₂ | Reaction of InCl₃, intermediate (II-17) and DBU in chloronaphthalene | 790 |
| I-38 | SiCl₂ | Reaction of SiCl₄ and intermediate (III-2) in quinoline | 745 |
| I-39 | Si(OH)₂ | Hydrolysis of compound (I-38) with aqueous ammonia | 745 |
| I-40 | Si(OCO—CH₃)₂ | Reaction of compound (I-39) and acetyl chloride in quinoline | 745 |
| I-41 | GeCl₂ | Reaction of GeCl₄ and intermediate (III-3) in quinoline | 778 |
| I-42 | Ge(OH)₂ | Hydrolysis of compound (I-41) with aqueous ammonia | 775 |
| I-43 | SnCl₂ | Reaction of SnCl₄ and intermediate (III-4) in quinoline | 799 |
| I-44 | Sn(OH)₂ | Hydrolysis of compound (I-43) with aqueous NaOH | 790 |

Example 45

A mixture of 240 parts of the phthalonitrile derivative represented by the following structural formula (II-33), 18 parts of cuprous chloride, 122 parts of DBU and 1,500 parts of n-amyl alcohol was heated at reflux for 5.5 hours:

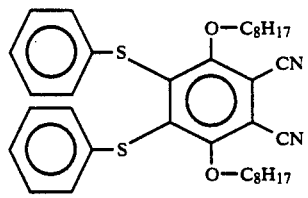

(II-33)

Afterward, methyl alcohol was added to the resulting reaction solution in order to precipitate crystals and the latter were collected by suction filtration and then purified through a column (hexane:benzene=1:1), so that 140 parts (yield 60%) of a phthalocyanine compound represented by the following structural formula (I-45) was obtained (λmax 778 nm/hexane; εmax $2.8 \times 10^5$):

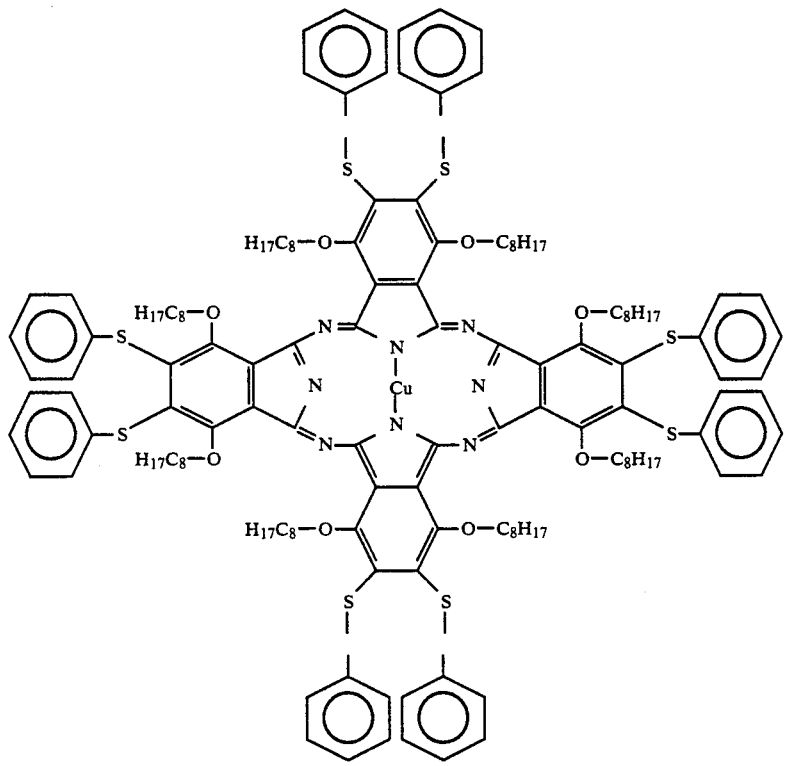

(I-45)

Results of elemental analysis (as Cu $C_{144}H_{176}N_8O_8S_8$):

| | C | H | N | S |
|---|---|---|---|---|
| Calcd. (%) | 70.11 | 7.19 | 4.54 | 10.40 |
| Found (%) | 70.08 | 7.13 | 4.52 | 10.36 |

Next, 1 part of the obtained phthalocyanine compound (I-45) was mixed with 100 parts of n-octane, and the resulting solution was applied onto a polycarbonate optical card substrate. Afterward, the applied substrate was coated with a resin to prepare an optical card. The thus-prepared card had a reflectance of 33% and a sensitivity (C/N ratio) of 50 dB at 830 nm, 8 mW and a linear velocity of 2.8 m/sec. In addition, the durability of the card was also good.

Moreover, 4 parts of the compound (I-45) was mixed with heating with 1,000 parts of polystyrene resin, and the mixture was then molded into the shape of a plate. The thus-obtained filter sufficiently absorbed rays at 750 to 850 nm.

Example 46

A mixture of 120 parts of the phthalonitrile derivative represented by the structural formula (II-33), 22 parts of acetylacetone vanadium, 61 parts of DBU and 750 parts of n-amyl alcohol was heated at reflux for 12 hours. After the solvent was distilled off, the resulting residue was then purified through a column (toluene), so that 19 parts (yield 15%) of the phthalocyanine compound represented by the following structural formula (I-46) was obtained ($\lambda$max 809 nm/hexane; $\epsilon$max $2.4 \times 10^5$):

18 parts of cuprous chloride, 122 parts of DBU and 1,500 parts of n-amyl alcohol was heated at reflux for 5.5 hours:

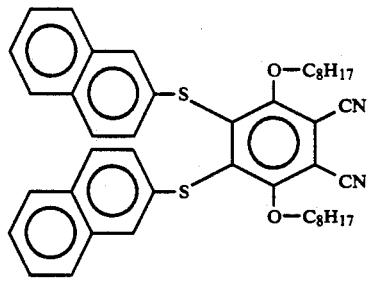

(II-34)

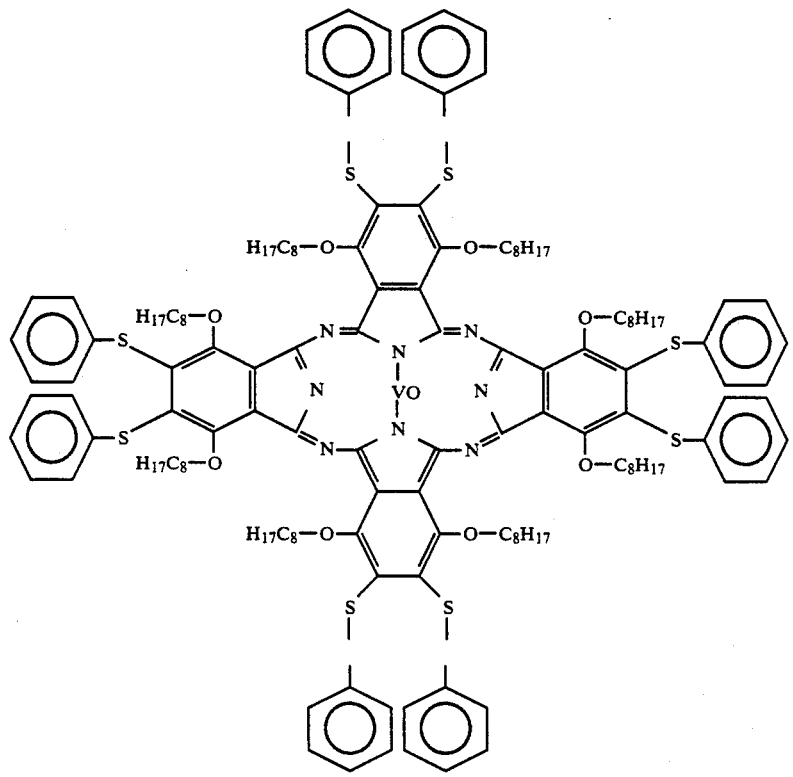

(I-46)

Results of elemental analysis (as V $C_{144}H_{176}N_8O_9S_8$):

|  | C | H | N | S |
|---|---|---|---|---|
| Calcd. (%) | 70.01 | 7.18 | 4.54 | 10.38 |
| Found (%) | 69.96 | 7.14 | 4.50 | 10.36 |

Example 47

A mixture of 280 parts of the phthalonitrile derivative represented by the following structural formula (II-34), Afterward, methyl alcohol was added to the resulting reaction solution in order to precipitate crystals, and the latter were collected by suction filtration and then purified through a column (toluene), so that 190 parts (yield 66%) of a phthalocyanine compound represented by the following structural formula (I-47) was obtained ($\lambda$max 787 nm/chloroform; $\epsilon$max $2.37 \times 10^5$):

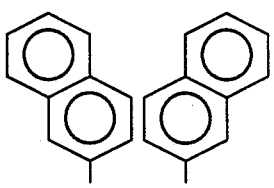

(I-47)

-continued

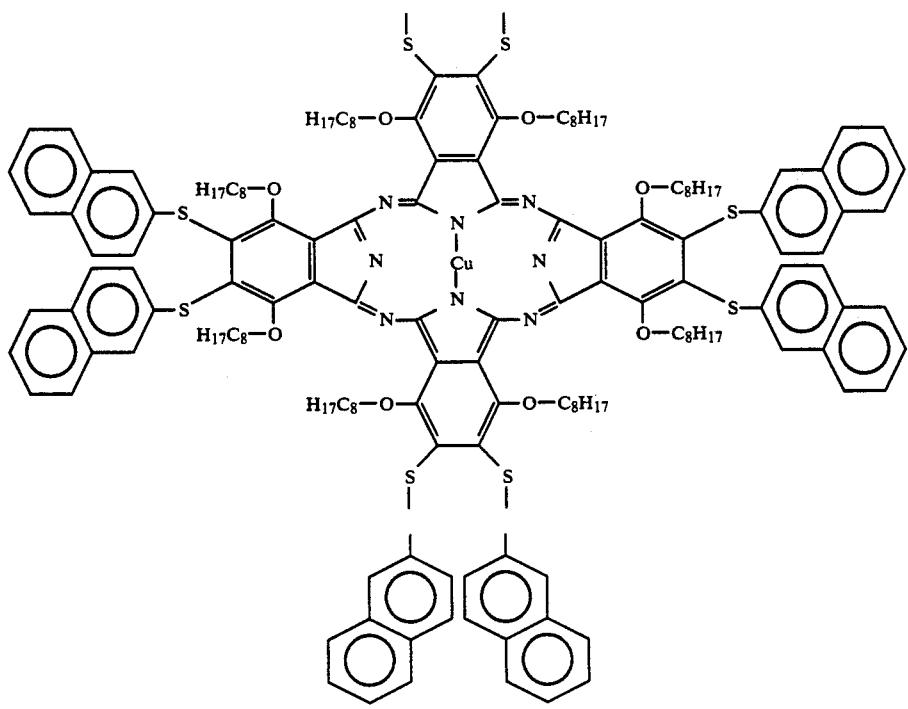

Results of elemental analysis (as Cu $C_{176}H_{192}N_8O_8S_8$):

|  | C | H | N | S |
|---|---|---|---|---|
| Calcd. (%) | 73.72 | 6.75 | 3.91 | 8.95 |
| Found (%) | 73.66 | 6.72 | 3.88 | 8.91 |

Example 48

A mixture of 140 parts of the phthalonitrile derivative represented by the structural formula (II-34), 22 parts of acetylacetone vanadium, 61 parts of DBU and 750 parts of n-amyl alcohol was heated at reflux for 12 hours. After the solvent was distilled off, the resulting residue was purified through a column (toluene), so that 35 parts (yield 25%) of a phthalocyanine compound represented by the following structural formula (I-48) was obtained (λmax 815 nm/hexane; εmax $2.4 \times 10^5$):

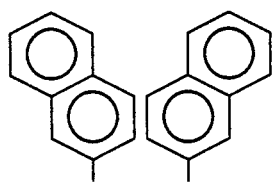

(I-47)

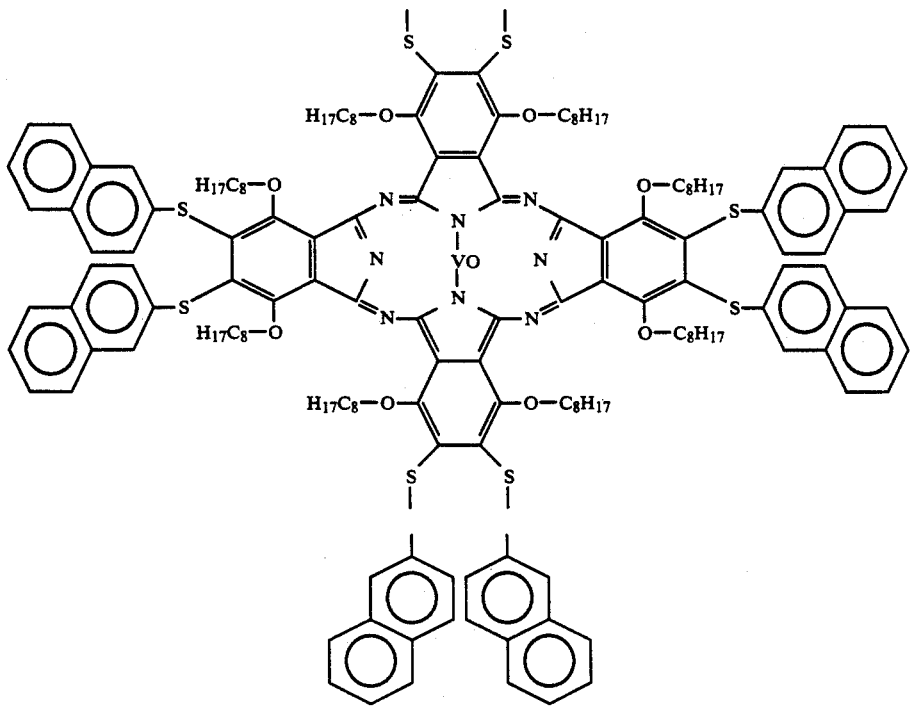

Results of elemental analysis (as V $C_{176}H_{192}N_8O_9S_8$):

|  | C | H | N | S |
|---|---|---|---|---|
| Calcd. (%) | 73.63 | 6.74 | 3.90 | 8.93 |
| Found (%) | 73.58 | 6.71 | 3.86 | 8.87 |

Example 49

A mixture of 413 parts of a phthalonitrile derivative represented by the following structural formula (II-35), 22 parts of 90% cuprous chloride, 244 parts of DBU and 2,500 parts of n-amyl alcohol was heated at reflux for 5 hours:

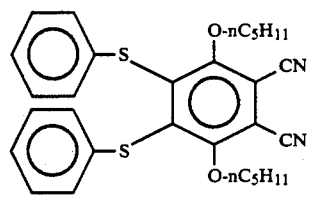
(II-35)

Afterward, the resulting reaction solution was poured into 2,400 parts of methyl alcohol in order to precipitate crystals, and the latter were collected by suction filtration and then purified through a column (silica gel/hexane:toluene=1:1), so that 260 parts (yield 61%) of a phthalocyanine compound represented by the following structural formula (I-49) was obtained (λmax 778 nm/hexane; εmax $2.5 \times 10^5$):

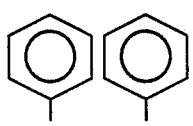
(I-49)

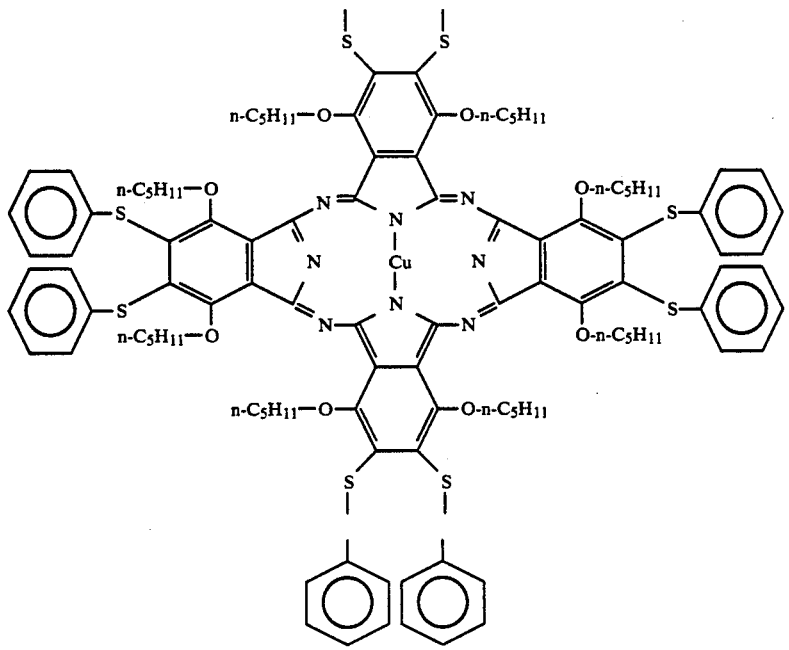

Results of elemental analysis (as Cu $C_{120}H_{128}N_8O_8S_8$):

|  | C | H | N | S |
|---|---|---|---|---|
| Calcd. (%) | 67.65 | 6.06 | 5.26 | 12.04 |
| Found (%) | 67.59 | 6.07 | 5.22 | 12.00 |

Next, 1 part of the obtained phthalocyanine compound (I-49) was dissolved in 100 parts of dibutyl ether, and the resulting solution was applied onto a polycarbonate optical disc substrate. The thus-prepared optical disc had a reflectance of 40% and a sensitivity of 51 dB at 830 nm, 8 mW and a linear velocity of 5.5 m/sec.

Moreover, 7 parts of the compound (I-49) was dissolved in 1,000 parts of a cyanobiphenyl liquid crystal mixture, and a liquid crystal panel was then prepared by using the solution. When an image was written on this panel by the use of a laser beam, it appeared distinctly thereon.

Moreover, 1 part of the phthalocyanine compound (I-49) was dissolved in 100 parts of dibutyl ether, and the resulting solution was then applied onto a polycarbonate optical card substrate. Afterward, the upper layer was further coated with a resin in order to prepare an optical card. The thus-prepared optical card had a reflectance of 40% and a sensitivity (C/N ratio) of 50 dB at 830 nm, 8 mW and a linear velocity of 2.8 m/sec. The durability of this card was also good.

Furthermore, 4 parts of the compound (I-49) was mixed with heating with 1,000 parts of polystyrene resin, and then molded into the shape of a plate. The thus-prepared filter sufficiently absorbed rays at 750 to 850 nm.

Example 50

A mixture of 464 parts of a phthalonitrile derivative represented by the following structural formula (II-36), 40 parts of 90% cuprous chloride, 247 parts of DBU and 2,800 parts of n-amyl alcohol was heated at reflux for 6 hours:

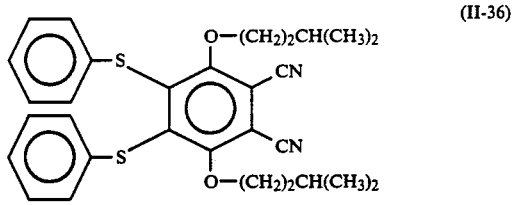

(II-36)

Afterward, the resulting reaction solution was poured into 3,160 parts of methyl alcohol in order to precipitate crystals, and the latter were collected by suction filtration and then purified through a column (silica gel/hexane:toluene = 1:1), so that 350 parts (yield 73%) of a phthalocyanine compound represented by the following structural formula (I-50) was obtained (λmax 778 nm/hexane; εmax $2.6 \times 10^5$):

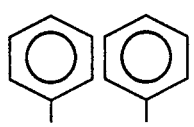

(I-50)

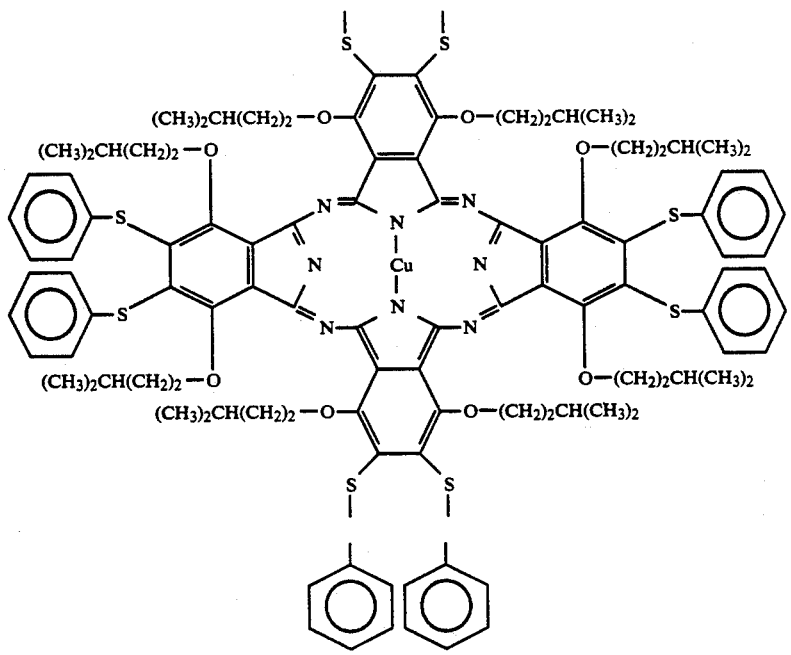

Results of elemental analysis (as Cu $C_{120}H_{128}N_8O_8S_8$):

|  | C | H | N | S |
|---|---|---|---|---|
| Calcd. (%) | 67.65 | 6.06 | 5.26 | 12.04 |
| Found (%) | 67.58 | 6.08 | 5.25 | 12.02 |

Next, 1 part of the obtained phthalocyanine compound (I-50) was dissolved in 100 parts of dibutyl ether, and the resulting solution was applied onto a polycarbonate optical disc substrate. The thus-prepared optical disc had a reflectance of 41% and a sensitivity of 50 dB at 830 nm, 8 mW and a linear velocity of 5.5 m/sec.

Moreover, 7 parts of the compound (I-50) was dissolved in 1,000 parts of a cyanobiphenyl liquid crystal mixture, and a liquid crystal panel was then prepared by using the solution. When an image was written on this panel by the use of a laser beam, it appeared distinctly thereon.

Moreover, 1 part of the phthalocyanine compound (I-50) was dissolved in 100 parts of dibutyl ether, and the resulting solution was then applied onto a polycarbonate optical card substrate. Afterward, the upper layer was further coated with a resin in order to prepare an optical card. The thus-prepared optical card had a reflectance of 41% and a sensitivity (C/N ratio) of 50 dB at 830 nm, 8 mW and a linear velocity of 2.8 m/sec. The durability of this card was also good.

Furthermore, 4 parts of the compound (I-50) was mixed with heating with 1,000 parts of polystyrene resin, and then molded into the shape of a plate. The thus-prepared filter sufficiently absorbed rays at 750 to 850 nm.

Example 51

A mixture of 377 parts of a phthalonitrile derivative represented by the following structural formula (II-37), 27 parts of 90% cuprous chloride, 182 parts of DBU and 1,900 parts of n-amyl alcohol was heated at reflux for 6 hours:

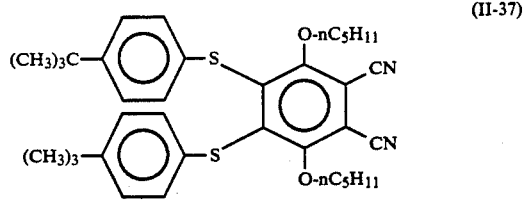

(II-37)

Afterward, the resulting reaction solution was poured into 3,200 parts of methyl alcohol in order to precipitate crystals, and the latter were collected by suction filtration and then purified through a column (silica gel/hexane:toluene=1:1), so that 270 parts (yield 70%) of a phthalocyanine compound represented by the following structural formula (I-51) was obtained (λmax 778 nm/hexane; εmax $2.82 \times 10^5$):

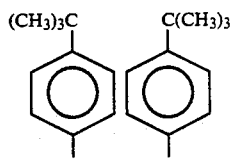

(I-51)

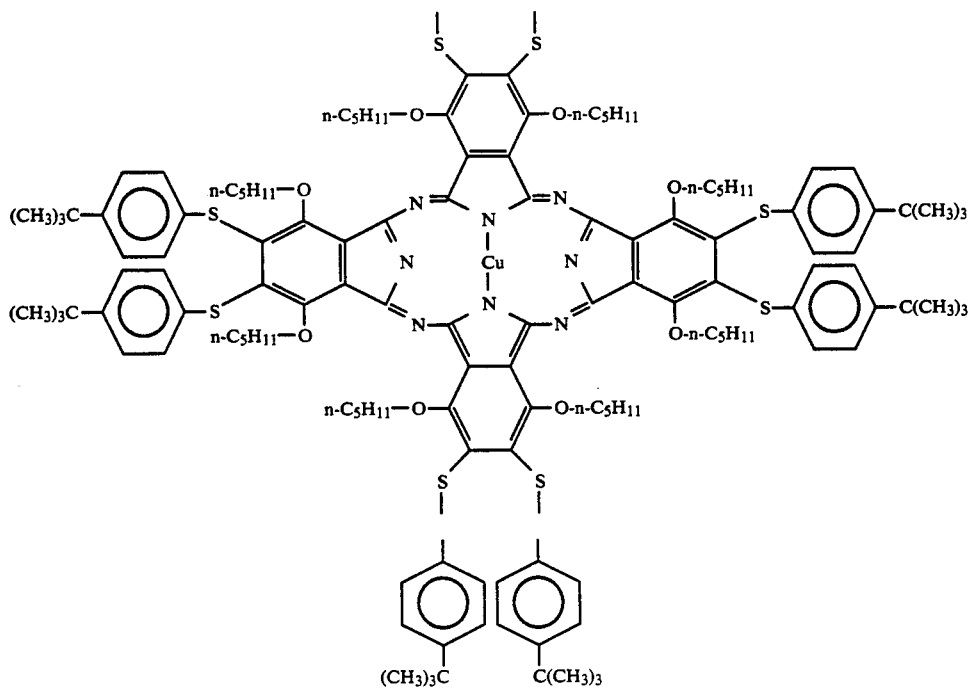

Results of elemental analysis (as Cu $C_{152}H_{192}N_8O_8S_8$):

|  | C | H | N | S |
|---|---|---|---|---|
| Calcd. (%) | 70.78 | 7.50 | 4.34 | 9.95 |
| Found (%) | 70.51 | 7.47 | 4.36 | 9.90 |

Next, 1 part of the obtained phthalocyanine compound (I-51) was dissolved in 100 parts of dibutyl ether, and the resulting solution was applied onto a polycarbonate optical disc substrate. The thus-prepared optical disc had a reflectance of 34% and a sensitivity of 51 dB at 830 nm, 8 mW and a linear velocity of 5.5 m/sec.

Moreover, 7 parts of the compound (I-51) was dissolved in 1,000 parts of a cyanobiphenyl liquid crystal mixture, and a liquid crystal panel was then prepared by using the solution. When an image was written on this panel by the use of a laser beam, it appeared distinctly thereon.

Moreover, 1 part of the phthalocyanine compound (I-51) was dissolved in 100 parts of dibutyl ether, and the resulting solution was then applied onto a polycarbonate optical card substrate. Afterward, the upper layer was further coated with a resin in order to prepare an optical card. The thus-prepared optical card had a reflectance of 34% and a sensitivity (C/N ratio) of 50 dB at 830 nm, 8 mW and a linear velocity of 2.8 m/sec. The durability of this card was also good.

Furthermore, 4 parts of the compound (I-51) was mixed with heating with 1,000 parts of polystyrene resin, and then molded into the shape of a plate. The thus prepared filter sufficiently absorbed rays at 750 to 850 nm.

Example 52

A mixture of 377 parts of a phthalonitrile derivative represented by the following structural formula (II-38), 27 parts of 90% cuprous chloride, 182 parts of DBU and 1,900 parts of n-amyl alcohol was heated at reflux for 6 hours:

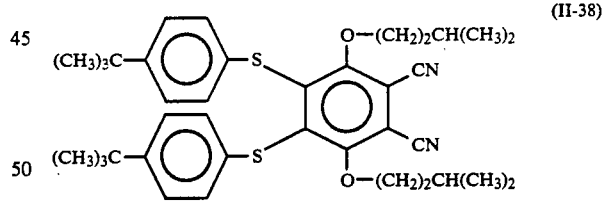

(II-38)

Afterward, the resulting reaction solution was poured into 3,200 parts of methyl alcohol in order to precipitate crystals, and the latter were collected by suction filtration and then purified through a column (silica gel/hexane:toluene=1:1), so that 290 parts (yield 75%) of a phthalocyanine compound represented by the following structural formula (I-52) was obtained (λmax 778 nm/hexane; εmax $2.66 \times 10^5$):

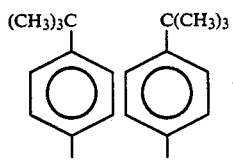

(I-52)

-continued

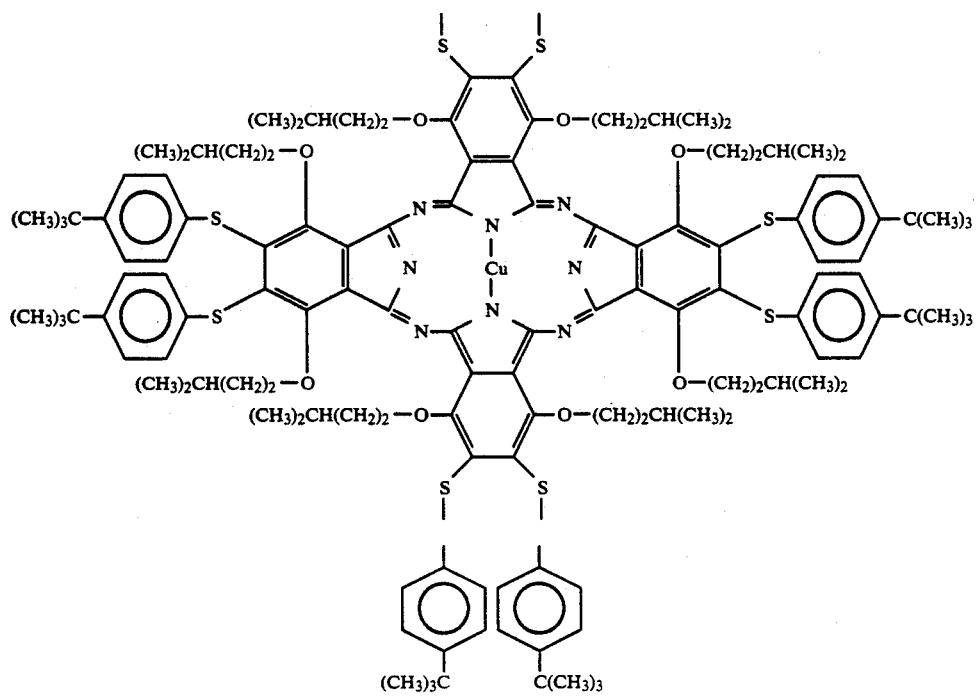

Results of elemental analysis (as $C_{152}H_{192}N_8O_8S_8$):

|  | C | H | N | S |
|---|---|---|---|---|
| Calcd. (%) | 70.78 | 7.50 | 4.34 | 9.95 |
| Found (%) | 70.59 | 7.48 | 4.33 | 9.89 |

Next, 1 part of the obtained phthalocyanine compound (I-52) was dissolved in 100 parts of dibutyl ether, and the resulting solution was applied onto a polycarbonate optical disc substrate. The thus-prepared optical disc had a reflectance of 34% and a sensitivity of 52 dB at 830 nm, 8 mW and a linear velocity of 5.5 m/sec.

Moreover, 7 parts of the compound (I-52) was dissolved in 1,000 parts of a cyanobiphenyl liquid crystal mixture, and a liquid crystal panel was then prepared by using the solution. When an image was written on this panel by the use of a laser beam, it appeared distinctly thereon.

Moreover, 1 part of the phthalocyanine compound (I-52) was dissolved in 100 parts of dibutyl ether, and the resulting solution was then applied onto a polycarbonate optical card substrate. Afterward, the upper layer was further coated with a resin in order to prepare an optical card. The thus-prepared optical card had a reflectance of 34% and a sensitivity (C/N ratio) of 50 dB at 830 nm, 8 mW and a linear velocity of 2.8 m/sec. The durability of this card was also good.

Furthermore, 4 parts cf the compound (I-52) was mixed with heating with 1,000 parts of polystyrene resin, and then molded into the shape of a plate. The thus-prepared filter sufficiently absorbed rays at 750 to 850 nm.

Example 53

A mixture of 43 parts Of $SiCl_4$ and 3,000 parts of quinoline was heated up to 200° C. To the heated mixture was added 533 parts of a diiminoisoindoline derivative represented by the following structural formula (III-7), and the solution was then heated at reflux for 5 hours:

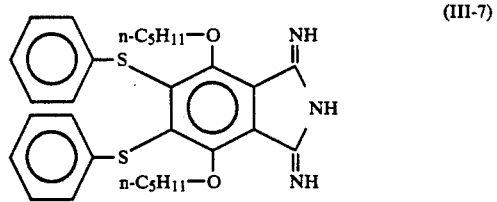

(III-7)

Afterward, the resulting reaction solution was poured into 3,500 parts of methyl alcohol in order to precipitate crystals, and the latter were collected by suction filtration and then washed with methanol, followed by drying, thereby obtaining 195 parts (yield 36%) of a phthalocyanine compound represented by the following structural formula (I-53) (λmax 780 nm/hexane; εmax $2.48 \times 10^5$):

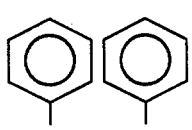

(I-53)

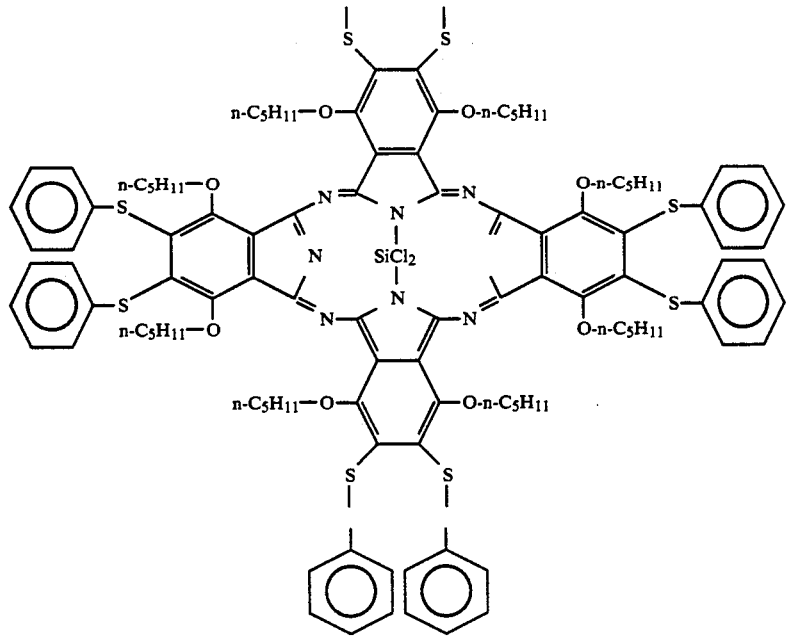

Results of elemental analysis (as Si $C_{120}H_{128}N_8O_8S_8Cl_2$):

|  | C | H | N | Cl | S |
|---|---|---|---|---|---|
| Calcd. (%) | 66.57 | 5.92 | 5.18 | 3.28 | 11.84 |
| Found (%) | 66.46 | 5.95 | 5.14 | 3.22 | 11.79 |

Next, 1 part of the obtained phthalocyanine compound (I-53) was dissolved in 100 parts of dibutyl ether, and the resulting solution was applied onto a polycarbonate optical disc substrate. The thus-prepared optical disc had a reflectance of 33% and a sensitivity of 50 dB (C/N ratio) at 780 nm, 8 mW and a linear velocity of 5.5 m/sec.

Moreover, 7 parts of the compound (I-53) was dissolved in 1,000 parts of a cyanobiphenyl liquid crystal mixture, and a liquid crystal panel was then prepared by using the solution. When an image was written on this panel by the use of a laser beam, it appeared distinctly thereon.

Moreover, 1 part of the phthalocyanine compound (I-53) was dissolved in 100 parts of dibutyl ether, and the resulting solution was then applied onto a polycarbonate optical card substrate. Afterward, the resulting recording layer was further coated with a resin in order to prepare an optical card. The thus-prepared optical card had a reflectance of 33% and a sensitivity (C/N ratio) of 50 dB at 780 nm, 8 mW and a linear velocity of 2.8 m/sec.

Furthermore, 4 parts of the compound (I-53) was mixed with heating with 1,000 parts of polystyrene resin, and then molded into the shape of a plate. The thus prepared filter sufficiently absorbed rays at 750 to 850 nm.

Examples 54 to 97

One to four kinds of phthalonitriles (Table 5) represented by the following formula (II) or diiminoisoindolines (Table 6) represented by the formula (III) were reacted with metal derivatives to synthesize the phthalocyanines shown in Table 7:

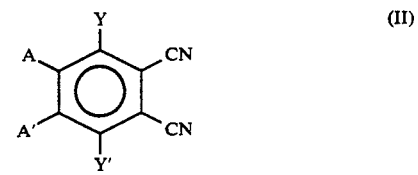

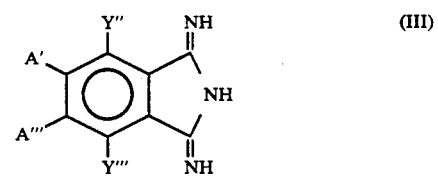

The synthesized compounds had great molecular extinction coefficients, and optical recording media made from these compounds were also excellent in reflectance, sensitivity and durability.

TABLE 5

| Intermediate | Y | Y' | A | A' |
|---|---|---|---|---|
| II-39 | —O-n-$C_5H_{11}$ | —O-n-$C_5H_{11}$ | —$SC_{10}H_7$ | —$SC_{10}H_7$ |
| II-40 | —O$(CH_2)_2$CH$(CH_3)_2$ | —O$(CH_2)_2$CH$(CH_3)_2$ | —$SC_{10}H_7$ | —$SC_{10}H_7$ |
| II-41 | —O-n-$C_5H_{11}$ | —O-n-$C_5H_{11}$ | —$SC_6H_5CH_3$ | —$SC_6H_5CH_3$ |
| II-42 | —O$(CH_2)_2$CH$(CH_3)_2$ | —O$(CH_2)_2(CH_3)_2$ | —$SC_6H_5CH_3$ | —$SC_6H_5CH_3$ |
| II-43 | —O-n-$C_5H_{11}$ | —O-n-$C_6H_{13}$ | —$SC_6H_5$ | —$SC_6H_5$ |
| II-44 | n-$C_8H_{17}$ | —$OC_6H_{13}$ | —Cl | —Cl |

TABLE 5-continued

| Intermediate | Y | Y' | A | A' |
|---|---|---|---|---|
| II-45 | —CH$_3$ | —OCH[CH(CH$_3$)$_2$]$_2$ | —I | —I |
| II-46 | neo-C$_5$H$_{11}$ | —OCH$_2$CH(C$_2$H$_5$)C$_4$H$_9$ | —C$_6$H$_5$ | —C$_6$H$_5$ |
| II-47 | n-C$_4$H$_9$ | —OCH$_2$CH(CH$_3$)CH$_2$CH$_2$C(CH$_3$)$_3$ | —SC$_6$H$_5$ | —SC$_6$H$_5$ |
| II-48 | —CH$_2$CH$_2$(CH$_3$)$_2$ | —OC$_6$H$_{13}$ | —CH$_2$CH$_2$CH(OCH$_3$)CH$_2$— | |
| II-49 | —CH$_3$ | —OC$_6$H$_{11}$(cyclo) | —CH$_2$CH$_2$CH$_2$CH$_2$— | |
| II-50 | n-C$_8$H$_{17}$ | —OCH$_2$CH$_2$C(CH$_3$)$_3$ | —H | —H |
| II-51 | CH$_2$CH$_2$C(C$_2$H$_5$)$_3$ | —OC$_6$H$_{13}$ | —CH$_2$C$_6$H$_5$ | —CH$_2$C$_6$H$_5$ |
| II-52 | —C$_4$H$_9$ | —OC$_8$H$_{17}$ | —OC$_6$H$_5$ | —OC$_6$H$_5$ |
| II-53 | —C$_3$H$_7$ | —OC$_{12}$H$_{25}$ | —OC$_6$H$_{11}$-cyclo | —OC$_6$H$_{11}$-cyclo |
| II-54 | CH$_3$S— | —OCH[CH(CH$_3$)$_2$]$_2$ | —H | —H |
| II-55 | —OCH[CH(CH$_3$)$_2$]$_2$ | —OCH[CH(CH$_3$)$_2$]$_2$ | —CH$_2$Cl | —CH$_2$Cl |
| II-56 | —H | —SCH[CH(CH$_3$)$_2$]$_2$ | —Cl | —Cl |
| II-57 | —OCH[CH(CH$_3$)$_2$]$_2$ | —SCH$_2$CH$_2$C(CH$_3$)$_3$ | —Cl | —Cl |
| II-58 | CH$_2$CH(CH$_3$)CH$_2$CH$_2$C(CH$_3$)$_3$ | —OC$_4$H$_9$(iso) | —H | —H |
| II-59 | —SCH$_2$CH(C$_2$H$_5$)C$_4$H$_9$ | —H | —H | —H |
| II-60 | —S—C$_5$H$_{11}$ | —H | —CH$_3$ | —CH$_3$ |
| II-61 | —CH$_3$ | —SCH[CH$_2$CH(CH$_3$)$_2$]$_2$ | —SCH$_2$CH$_2$S— | |
| II-62 | —OCH[CH$_2$CH(CH$_3$)$_2$]$_2$ | —H | —CH$_2$CH$_2$CH$_2$CH$_2$— | |
| II-63 | —OCH[CH$_2$CH(CH$_3$)$_2$]$_2$ | —H | —OC$_6$H$_5$ | —OC$_6$H$_5$ |
| II-64 | —OC$_8$H$_{17}$ | —OCH[CH(CH$_3$)$_2$]$_2$ | —C$_6$H$_5$ | —C$_6$H$_5$ |
| II-65 | —OC$_8$H$_{17}$ | —OC$_6$H$_{10}$(CH$_3$)(cyclo) | —CH$_2$OCH$_3$ | —CH$_2$OCH$_3$ |
| II-66 | —OC$_8$H$_{17}$ | —OC$_8$H$_{17}$ | —C$_{10}$H$_7$ | —C$_{10}$H$_7$ |
| II-67 | —OCH$_2$CH(C$_2$H$_5$)C$_4$H$_9$ | —OCH$_2$CH(C$_2$H$_5$)C$_4$H$_9$ | —SC$_6$H$_5$ | —SC$_6$H$_5$ |
| II-68 | —OCH$_2$CHCH$_2$CH$_2$C(CH$_3$)$_3$<br>\|<br>CH$_3$ | —OCH$_2$CHCH$_2$CH$_2$C(CH$_3$)$_3$<br>\|<br>CH$_3$ | —SC$_6$H$_5$ | —SC$_6$H$_5$ |

TABLE 6

| Intermediate | Y'' | Y''' | A'' | A''' |
|---|---|---|---|---|
| III-8 | —O(CH$_2$)$_2$CH(CH$_3$)$_2$ | —O(CH$_2$)$_2$CH(CH$_3$)$_2$ | —SC$_{10}$H$_7$ | —SC$_{10}$H$_7$ |
| III-9 | —OC$_8$H$_{17}$ | —OC$_8$H$_{17}$ | —SC$_6$H$_5$ | —SC$_6$H$_5$ |
| III-10 | C$_2$H$_5$<br>\|<br>—OCH$_2$CHC$_4$H$_9$ | C$_2$H$_5$<br>\|<br>—OCH$_2$CHC$_4$H$_9$ | —SC$_{10}$H$_7$ | —SC$_{10}$H$_7$ |
| III-11 | —OC$_6$H$_{13}$ | —OC$_6$H$_{13}$ | —SC$_6$H$_4$C$_4$H$_9$ | —SC$_6$H$_4$C$_4$H$_9$ |

TABLE 7

| Compound | Central Metal | Manufacturing Process | λmax |
|---|---|---|---|
| I-54 | Ni | Reaction of DBU, NiCl$_2$ and intermediate (II-38) in amyl alcohol | 780 |
| I-55 | Fe | Reaction of DBU, FeCl$_2$ and intermediate (II-36) in amyl alcohol | 770 |
| I-56 | Zn | Reaction of DBU, Zn(OAc)$_2$ and intermediate (II-41) in amyl alcohol | 781 |
| I-57 | VO | Reaction of DBU, VO(acac)$_2$ and intermediate (II-36) in amyl alcohol | 809 |
| I-58 | Mn(OH) | Reaction of DBU, MnCl$_2$ and intermediate (II-35) in amyl alcohol | 830 |
| I-59 | Pb | Reaction of DBU, Pb(OAc)$_2$ and intermediate (II-42) in amyl alcohol | 820 |
| I-60 | Si(OH)$_2$ | Hydrolysis of compound (I-53) with aqueous ammonia | 780 |
| I-61 | Cu | Reaction of DBU, CuCl and intermediate (II-39) in amyl alcohol | 787 |
| I-62 | Cu | Reaction of DBU, CuCl and intermediate (II-40) in amyl alcohol | 787 |
| I-63 | Cu | Reaction of DBU, CuCl and intermediate (II-42) in amyl alcohol | 778 |
| I-64 | Cu | Reaction of DBU, CuCl and intermediate (II-43) in amyl alcohol | 778 |
| I-65 | SiCl$_2$ | Reaction of SiCl$_4$ and intermediate (III-8) in quinoline | 780 |
| I-66 | VO | Reaction of DBU, VO(acac)$_2$ and intermediate (II-44) in amyl alcohol | 745 |
| I-67 | VO | Reaction of DBU, VO(acac)$_2$ and intermediate (II-45) in amyl alcohol | 760 |
| I-68 | VO | Reaction of DBU, VO(acac)$_2$ and intermediate (II-46) in amyl alcohol | 758 |
| I-69 | Cu | Reaction of DBU, CuCl and intermediate (II-47) in amyl alcohol | 760 |
| I-70 | VO | Reaction of DBU, VCl$_3$ and intermediate (II-48) in chloronaphthalene | 762 |
| I-71 | VO | Reaction of DBU, VCl$_3$ and intermediate (II-49) in chloronaphthalene | 760 |
| I-72 | Mn(OH) | Reaction of DBU, MnCl$_2$ and intermediate (II-50) in amyl alcohol | 760 |
| I-73 | Ni | Reaction of DBU, NiCl$_2$ and intermediate (II-51) in amyl alcohol | 735 |
| I-74 | Fe | Reaction of DBU, FeCl$_2$ and intermediate (II-52) in amyl alcohol | 745 |
| I-75 | Pb | Reaction of DBU, Pb(OAc)$_2$ and intermediate (II-53) in amyl alcohol | 780 |
| I-76 | VO | Reaction of DBU, VCl$_3$ and | 720 |

TABLE 7-continued

| Compound | Central Metal | Manufacturing Process | λmax |
|---|---|---|---|
| I-77 | VO | intermediate (II-54) in chloronaphthalene | |
| | | Reaction of DBU, VO(acac)₂ and intermediate (II-55) in amyl alcohol | 780 |
| I-78 | InCl | Reaction of DBU, InCl₃ and intermediate (II-56) in chloronaphthalene | 760 |
| I-79 | Zn | Reaction of DBU, Zn(OAc)₂ and intermediate (II-57) in amyl alcohol | 765 |
| I-80 | VO | Reaction of DBU, VCl₃ and intermediate (II-58) in chloronaphthalene | 750 |
| I-81 | VO | Reaction of DBU, VCl₃ and intermediate (II-59) in chloronaphthalene | 745 |
| I-82 | VO | Reaction of DBU, VCl₃ and intermediate (II-60) in chloronaphthalene | 795 |
| I-83 | Cu | Reaction of DBU, CuCl and intermediate (II-61) in amyl alcohol | 780 |
| I-84 | VO | Reaction of DBU, VCl₃ and intermediate (II-62) in chloronaphthalene | 745 |
| I-85 | VO | Reaction of DBU, VCl₃ and intermediate (II-63) in chloronaphthalene | 785 |
| I-86 | VO | Reaction of DBU, VCl₃ and intermediate (II-64) in chloronaphthalene | 780 |
| I-87 | VO | Reaction of DBU, VCl₃ and intermediate (II-65) in chloronaphthalene | 785 |
| I-88 | VO | Reaction of DBU, VCl₃ and intermediate (II-66) in chloronaphthalene | 780 |
| I-89 | Cu | Reaction of DBU, CuCl and intermediate (II-67) in amyl alcohol | 785 |
| I-90 | Cu | Reaction of DBU, CuCl and intermediate (II-68) in amyl alcohol | 789 |
| I-91 | SiCl₂ | Reaction of SiCl₄ and intermediate (III-9) in quinoline | 780 |
| I-92 | Si(OH)₂ | Hydrolysis of compound (I-91) with aqueous ammonia | 780 |
| I-93 | GeCl₂ | Reaction of GeCl₄ and intermediate (III-10) in quinoline | 778 |
| I-94 | Ge(OH)₂ | Hydrolysis of compound (I-93) with aqueous ammonia | 780 |
| I-95 | Si(OCOCH₃)₂ | Reaction of compound (I-92) and acetyl chloride in quinoline | 810 |
| I-96 | SnCl₂ | Reaction of SnCl₄ and intermediate (III-11) in quinoline | 800 |
| I-97 | Sn(OH)₂ | Hydrolysis of compound (I-96) with aqueous NaOH | 780 |

Example 98

A mixture of 10 parts of a phthalonitrile derivative represented by the following structural formula (II-69), 2 parts of PdCl₂, 4 parts of DBU and 200 parts of n-amyl alcohol was heated at reflux:

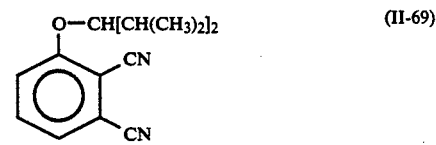

Afterward, the resulting reaction solution was poured into water, and the deposited tar was purified through column chromatography, so that 2 parts of a phthalocyanine compound represented by the following structural formula (I-98) was obtained (λmax 692 nm/hexane; εmax $2.5 \times 10^5$):

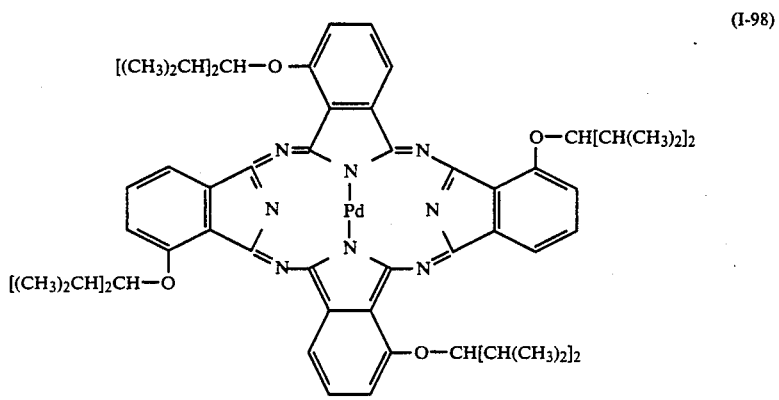

Results of elemental analysis (as Pd $C_{60}H_{72}N_8O_4$):

| | C | H | N |
|---|---|---|---|
| Calcd. (%) | 67.88 | 6.43 | 10.39 |
| Found (%) | 67.00 | 6.75 | 10.42 |

Next, 1 part of the obtained phthalocyanine compound (I-98) was dissolved in 100 parts of methylcyclohexane, and the resulting solution was then applied onto a polycarbonate substrate. Afterward, gold was sputtered thereon, and a UV setting resin was further applied and cured thereon, thereby preparing a CD-WORM type optical recording medium.

The thus-prepared CD-WORM type optical recording medium had a reflectance of 72% and a sensitivity of 52 dB at 8 mW and a linear velocity of 2.5 m/sec.

Moreover, the compound (I-98) was applied onto polycarbonate to prepare a film thereon. This film had high refractive indexes, i.e., 2.78 (at 720 nm), 2.05 (at 780 nm) and 1.95 (at 830 nm).

Example 99

A mixture of 10 parts of a phthalonitrile derivative represented by the following structural formula (II-70), 2 parts of PdCl$_2$, 4 parts of DBU and 200 parts of n-amyl alcohol was heated at reflux:

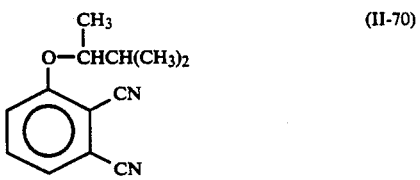
(II-70)

Afterward, the resulting reaction solution was poured into water, and the deposited tar was purified through column chromatography, so that 2.5 parts of a phthalocyanine compound represented by the following structural formula (I-99) was obtained (λmax 686 nm/hexane; εmax 2.5×10$^5$):

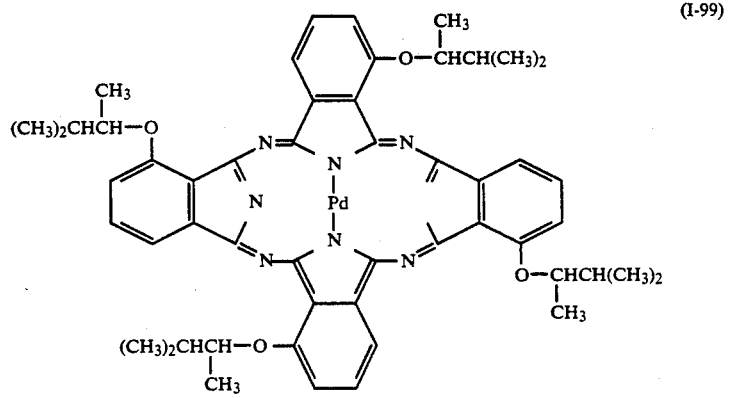
(I-99)

Results of elemental analysis (as Pd C$_{52}$H$_{52}$N$_8$O$_4$)

|  | C | H | N |
|---|---|---|---|
| Calcd. (%) | 64.83 | 5.86 | 11.68 |
| Found (%) | 64.90 | 5.80 | 11.60 |

Next, 1 part of the obtained phthalocyanine compound (I-99) was dissolved in 100 parts of methylcyclohexane, and the resulting solution was then applied onto a polycarbonate substrate. Afterward, an acrylic UV setting resin was further applied and cured thereon, thereby preparing an optical card.

The thus-prepared optical card had a reflectance of 28% and a sensitivity of 50 dB at 8 mW and a linear velocity of 1.8 m/sec.

Moreover, the compound (I-99) was applied onto polycarbonate to prepare a film thereon. This film had high refractive indexes, i.e., 2.37 (at 720 nm), 2.01 (at 780 nm) and 1.89 (at 830 nm).

Example 100

Following the same procedure as in Example 99, a compound having the structural formula (II-71)

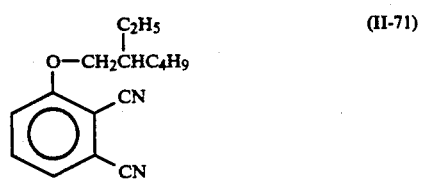
(II-71)

was reacted to obtain a compound represented by the following formula (I-100) (λmax 720 nm/hexane; εmax 2.01×10$^5$):

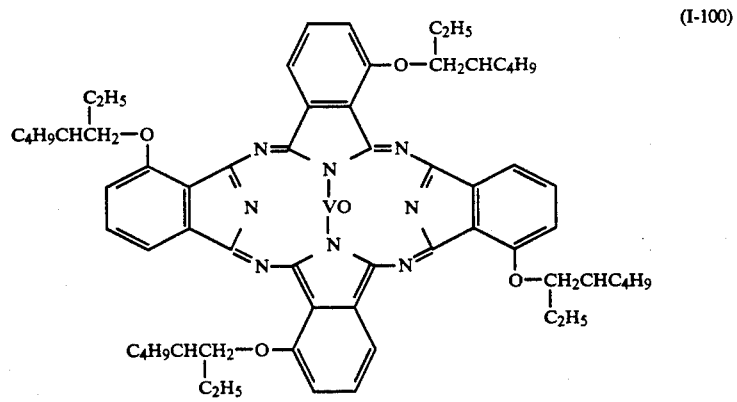
(I-100)

This compound (I-100) was applied onto polycarbonate to prepare a film thereon. This film had high refractive indexes, i.e., 1.96 (at 780 nm) and 1.86 (at 830 nm).

Moreover, 4 parts of the compound (I-100) was heated and melted together with 1000 parts of poly(methyl methacrylate) (PMMA) resin, and the mixture was then stretched in order to prepare a film having a thickness of 200 μm. The thus-prepared film sufficiently absorbed rays at 700 to 830 nm.

Example 101

A mixture of 10 parts of a phthalonitrile derivative represented by the following structural formula (II-72), 2 parts of $NiCl_2$, 4 parts of DBU and 200 parts of n-amyl alcohol was heated at reflux:

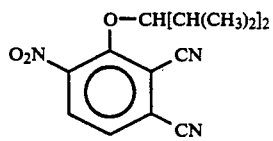
(II-72)

Afterward, the resulting reaction solution was poured into water, and the deposited tar was purified through column chromatography, so that 2 parts of a phthalocyanine compound represented by the following structural formula (I-101) was obtained (λmax 690 nm/hexane; εmax $2.4 \times 10^5$):

sputtered thereon, and a UV setting resin was further applied and cured thereon, thereby preparing a CD-WORM type optical recording medium.

The thus-prepared CD-WORM type optical recording medium had a reflectance of 71% and a sensitivity of 52 dB at 7 mW and a linear velocity of 1.5 m/sec.

Moreover, the compound (I-101) was applied onto polycarbonate to prepare a film thereon. This film had high refractive indexes, i.e., 2.65 (at 718 nm), 2.08 (at 780 nm) and 1.94 (at 830 nm).

Example 102

A mixture of 10 parts of a phthalonitrile derivative represented by the following structural formula (II-73), 2 parts of $PdCl_2$, 4 parts of DBU and 200 parts of n-amyl alcohol was heated at reflux:

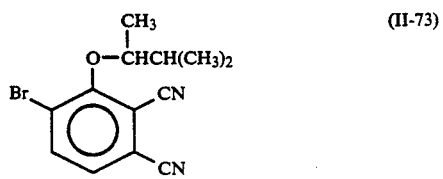
(II-73)

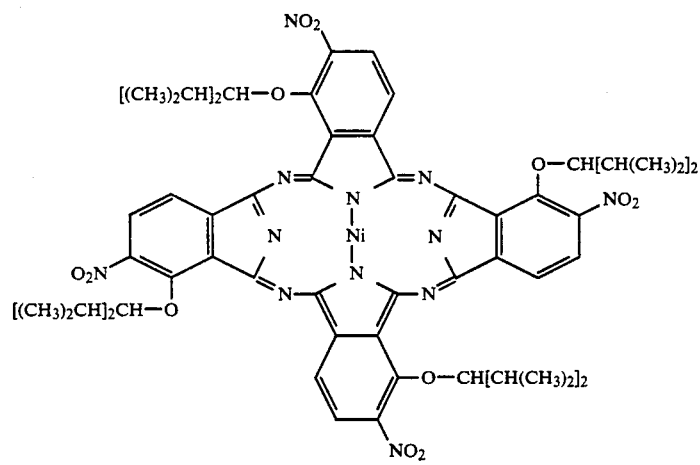
(I-101)

Results of elemental analysis (as Ni $C_{60}H_{68}N_{12}O_{12}$):

|  | C | H | N |
|---|---|---|---|
| Calcd. (%) | 59.66 | 5.63 | 13.92 |
| Found (%) | 60.01 | 5.75 | 14.02 |

Next, 1 part of the obtained phthalocyanine compound (I-101) was dissolved in 100 parts of methylcyclohexane, and the resulting solution was then applied onto a polycarbonate substrate. Afterward, gold was Afterward, the resulting reaction solution was poured into water, and the deposited tar was purified through column chromatography, so that 2.5 parts of a phthalocyanine compound represented by the following structural formula (I-102) was obtained (λmax 688 nm/hexane; εmax $2.4 \times 10^5$):

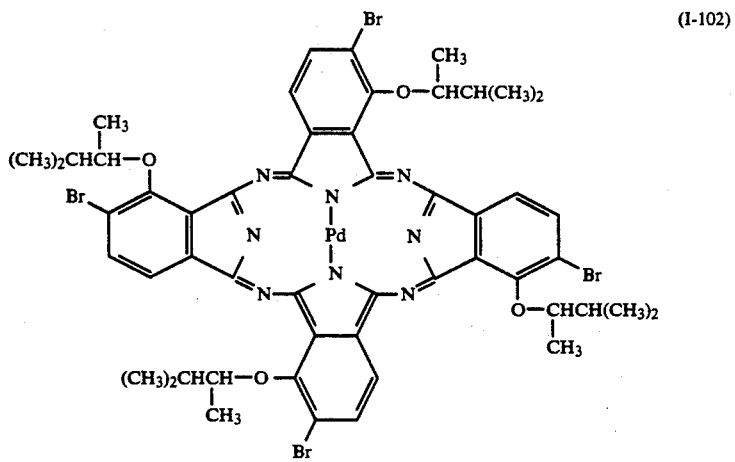

(I-102)

Results of elemental analysis (as Pd $C_{52}H_{52}N_8O_4Br_4$):

|   | C | H | N |
|---|---|---|---|
| Calcd. (%) | 64.90 | 5.50 | 11.60 |
| Found (%) | 65.10 | 5.46 | 11.68 |

Next, 1 part of the obtained phthalocyanine compound (I-102) was dissolved in 100 parts of methylcyclohexane, and the resulting solution was then applied onto a polycarbonate substrate. Afterward, an acrylic UV setting resin was further applied and cured thereon, thereby preparing an optical card.

This optical card had a reflectance of 32% and a sensitivity of 50 dB at 780 nm, 8 mW and a linear velocity of 1.8 m/sec.

Moreover, the compound (I-102) was applied onto polycarbonate to prepare a film thereon. This film had high refractive indexes, i.e., 2.40 (at 720 nm), 2.02 (at 780 nm) and 1.88 (at 830 nm).

Example 103

To 200 parts of acetic acid was added 10 parts of phthalocyanine of the above-mentioned formula (I-99), and 3 parts of fuming nitric acid (d=1.68) was further added thereto dropwise. The solution was reacted at room temperature for 1 hour and at 50° C. for 2 hours, thereby obtaining 8 parts of a phthalocyanine having the following structural formula ($\lambda$max 682 nm/hexane; $\epsilon$max $2.03 \times 10^5$):

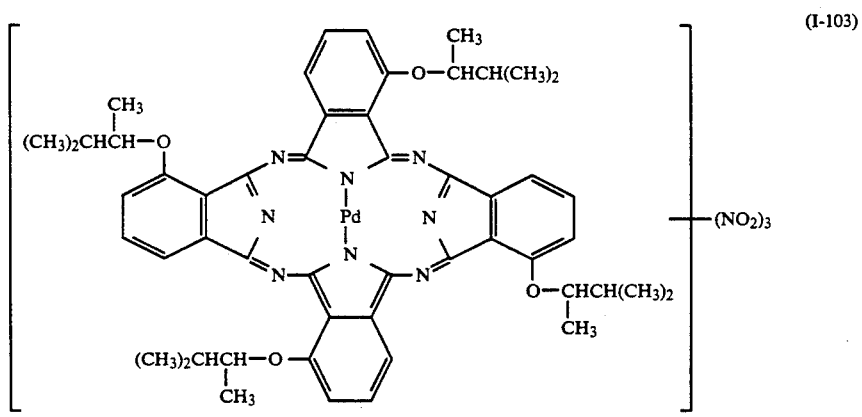

(I-103)

Next, 1 part of the obtained phthalocyanine compound (I-103) was dissolved in 100 parts of methylcyclohexane, and the resulting solution was then applied onto a polycarbonate substrate. Afterward, an acrylic UV setting resin was further applied and cured thereon, thereby preparing an optical card.

The thus prepared optical card had a reflectance of 28% and a sensitivity of 50 dB at 780 nm, 8 mW and a linear velocity of 1.8 m/sec.

Moreover, the compound (I-103) was applied onto polycarbonate to prepare a film thereon. This film had high refractive indexes, i.e., 2.47 (at 720 nm), 2.22 (at 780 nm) and 1.89 (at 830 nm).

Comparative Example 4

(Example XIX in Japanese Patent Laid-open Publication No. 39,286/1987)

In 100 parts of CELLOSOLVE ® 2-ethoxyethanol was dissolved 1 part of a compound represented by the following structural formula (A), and the resulting solution was then applied onto a polycarbonate substrate:

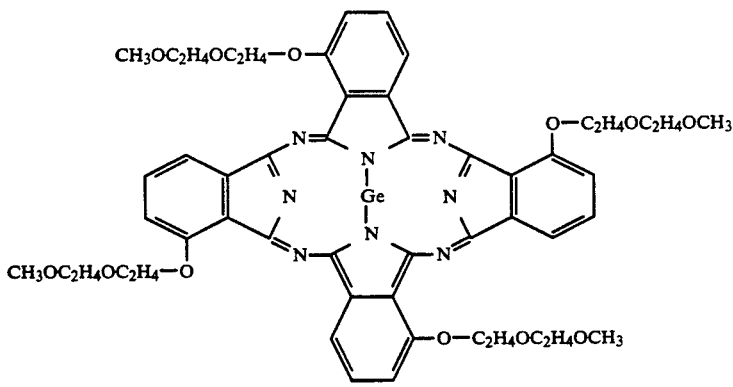

(A)

Afterward, gold was sputtered on the substrate, and a UV setting resin was further applied and cured thereon, thereby preparing a CD-WORM type optical medium.

The thus-prepared medium had a reflectance of 50% and the C/N ratio was 30 dB at 8 mW, 780 nm and a linear velocity of 2.5 m/sec.

Moreover, a film was made of the above-mentioned compound (A), and the refractive index of this film was 1.70 (at 780 nm).

Comparative Example 5

(Example VIII in Japanese Patent Laid-open Publication No. 39,286/1987)

Four parts of a compound represented by the structural formula (B)

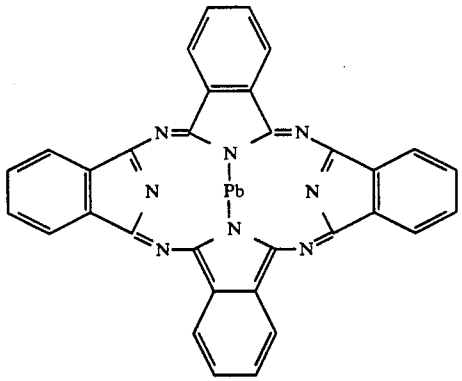

(B)

was heated and melted together with 1,000 parts of PMMA resin, and the mixture was then stretched in order to prepare a film having a thickness of 200 μm. At this time, it was confirmed that the above compound was thermally decomposed.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A near infrared absorber having a molecular extinction coefficient of 200,000 or more and represented by the formula (I)

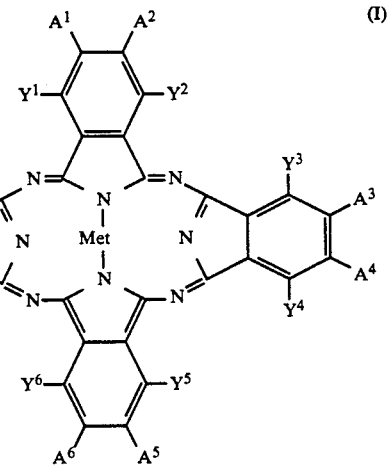

(I)

wherein one of each pair of $Y^1$ and $Y^2$, $Y^3$ and $Y^4$, and $Y^5$ and $Y^6$, and $Y^7$ and $Y^8$ is a branched or cyclic alkoxy group having 4 to 9 carbon atoms and the other is a straight-chain alkoxy group having 4 to 9 carbon atoms or a straight-chain alkylthio group having 4 to 9 carbon atoms; each of $A^1$, $A^2$, $A^3$, $A^4$, $A^5$, $A^6$, $A^6$ and $A^8$ is independently a hydrogen atom, a halogen atom, a nitro group, a straight-chain, branched or cyclic alkyl group having 1 to 10 carbon atoms, an aralkyl group having 7 to 20 carbon atoms, an alkenyl group having 2 to 10 carbon atoms, an alkynyl group having 2 to 10 carbon atoms, a straight-chain or branched alkoxy group having 1 to 4 carbon atoms, or a cyclic alkoxy group having 6 to 10 carbon atoms, an aryloxy group having 6 to 20 carbon atoms, a straight-chain, branched or cyclic alkylthio group having 1 to 10 carbon atoms, or an arylthio group having 6 to 20 carbon atoms; each pair of $A^1$ and $A^2$, $A^3$ and $A^4$, $A^5$ and $A^6$, and $A^7$ and $A^8$ may be bound together so as to form a ring; and Met represents two hydrogen atoms, a divalent metal atom, a trivalent monosubstituted or tetravalent disubstituted metal atom, or an oxymetal group.

2. An optical recording medium, comprising a recording layer which comprises a near infrared absorber having a molecular extinction coefficient of 200,000 or more and represented by the formula (I)

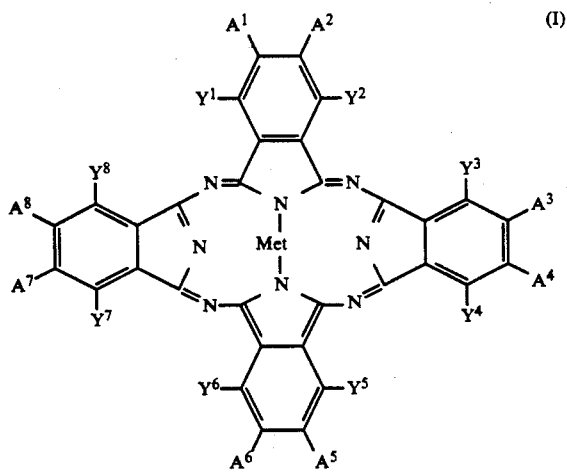

wherein one of each pair of $Y^1$ and $Y^2$, $Y^3$ and $Y^4$, $Y^5$ and $Y^6$, and $Y^7$ and $Y^8$ is a branched or cyclic alkoxy group having 4 to 9 carbon atoms and the other is a straight-chain alkoxy group having 4 to 9 carbon atoms or a straight-chain alkylthio group having 4 to 9 carbon atoms; each of $A^1$, $A^2$, $A^3$, $A^4$, $A^5$, $A^6$, $A^7$ and $A^8$ is independently a hydrogen atom, a halogen atom, a nitro group, a straight-chain, branched or cyclic alkyl group having 1 to 10 carbon atoms, an aralkyl group having 7 to 20 carbon atoms, an alkenyl group having 2 to 10 carbon atoms, an alkynyl group having 2 to 10 carbon atoms, a straight-chain or branched alkoxy group having 1 to 4 carbon atoms, or a cyclic alkoxy group having 6 to 10 carbon atoms, an aryloxy group having 6 to 20 carbon atoms, a straight-chain, branched or cyclic alkylthio group having 1 to 10 carbon atoms, or an arylthio group having 6 to 20 carbon atoms; each pair of $A^1$ and $A^2$, $A^3$ and $A^4$, $A^5$ and $A^6$, and $A^7$ and $A^8$ may be bound together so as to form a ring; and Met represents two hydrogen atoms, a divalent metal atom, a trivalent monosubstituted or tetravalent disubstituted metal atom, or an oxymetal group.

3. A liquid crystal element comprising a near infrared absorber having a molecular extinction coefficient of 200,000 or more and represented by the formula (I)

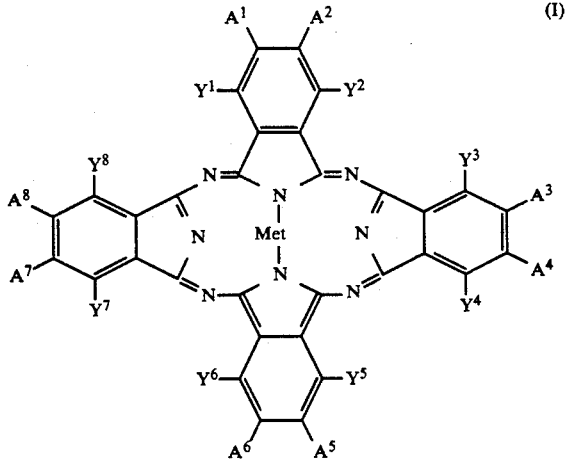

wherein one of each pair of $Y^1$ and $Y^2$, $Y^3$ and $Y^4$, $Y^5$ and $Y^6$, and $Y^7$ and $Y^8$ is a branched or cyclic alkoxy group having 4 to 9 carbon atoms and the other is a straight-chain alkoxy group having 4 to 9 carbon atoms or a straight-chain alkylthio group having 4 to 9 carbon atoms; each of $A^1$, $A^2$, $A^3$, $A^4$, $A^5$, $A^6$, $A^7$ and $A^8$ is independently a hydrogen atom, a halogen atom, a nitro group, a straight-chain, branched or cyclic alkyl group having 1 to 10 carbon atoms, an aralkyl group having 7 to 20 carbon atoms, an alkenyl group having 2 to 10 carbon atoms, an alkynyl group having 2 to 10 carbon atoms, a straight-chain or branched alkoxy group having 1 to 4 carbon atoms, or a cyclic alkoxy group having 6 to 10 carbon atoms, an aryloxy group having 6 to 20 carbon atoms, a straight-chain, ranched or cyclic alkylthio group having 1 to 10 carbon atoms, or an arylthio group having 6 to 20 carbon atoms; each pair of $A^1$ and $A^2$, $A^3$ and $A^4$, $A^5$ and $A^6$, and $A^7$ and $A^8$ may be bound together so as to form a ring; and Met represents two hydrogen atoms, a divalent metal atom, a trivalent monosubstituted or tetravalent disubstituted metal atom, or an oxymetal group.

4. A near infrared absorption filter comprising a near infrared absorber having a molecular extinction coefficient of 200,000 or more and represented by the formula (I)

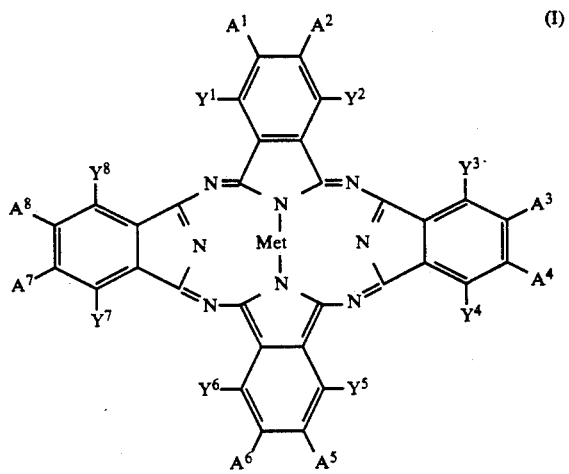

wherein one of each pair of $Y^1$ and $Y^2$, $Y^3$ and $Y^4$, $Y^5$ and $Y^6$, and $Y^7$ and $Y^8$ is a branched or cyclic alkoxy group having 4 to 9 carbon atoms and the other is a straight-chain alkoxy group having 4 to 9 carbon atoms or a straight-chain alkylthio group having 4 to 9 carbon atoms; each of $A^1$, $A^2$, $A^3$, $A^4$, $A^5$, $A^6$, $A^7$ and $A^8$ is independently a hydrogen atom, a halogen atom, a nitro group, a straight-chain, branched or cyclic alkyl group having 1 to 10 carbon atoms, an aralkyl group having 7 to 20 carbon atoms, an alkynyl group having 2 to 10 carbon atoms, an alkynyl group having 2 to 10 carbon atoms, a straight-chain or branched alkoxy group having 1 to 4 carbon atoms, or a cyclic alkoxy group having 6 to 10 carbon atoms, an aryloxy group having 6 to 20 carbon atoms, a straight-chain, branched or cyclic alkylthio group having 1 to 10 carbon atoms, or an arylthio group having 6 to 20 carbon atoms; each pair of $A^1$ and $A^2$, $A^3$ and $A^4$, $A^5$ and $A^6$, and $A^7$ and $A^8$ may be bound together so as to form a ring; and Met represents two hydrogen atoms, a divalent metal atom, a trivalent monosubstituted or tetravalent disubstituted metal atom, or an oxymetal group.

5. An optical card, comprising a recording layer which comprises a near infrared absorber having a molecular extinction coefficient of 200,000 or more and represented by the formula (I)

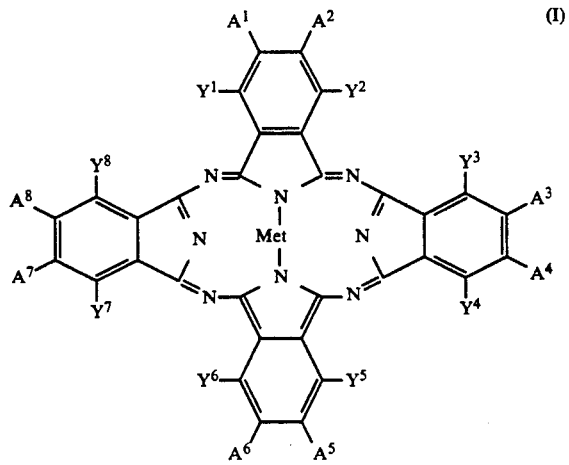

(I)

wherein one of each pair of $Y^1$ and $Y^2$, $Y^3$ and $Y^4$, $Y^5$ and $Y^6$, and $Y^7$ and $Y^8$ is a branched or cyclic alkoxy group having 4 to 9 carbon atoms and the other is a straight-chain alkoxy group having 4 to 9 carbon atoms or a straight-chain alkylthio group having 4 to 9 carbon atoms; each of $A^1$, $A^2$, $A^3$, $A^4$, $A^5$, $A^6$, $A^7$ and $A^8$ is independently a hydrogen atom, a halogen atom, a nitro group, a straight-chain, branched or cyclic alkyl group having 1 to 10 carbon atoms, an aralkyl group having 7 to 20 carbon atoms, an alkenyl group having 2 to 10 carbon atoms, an alkynyl group having 2 to 10 carbon atoms, a straight-chain or branched alkoxy group having 1 to 4 carbon atoms or a cyclic alkoxy group having 6 to 10 carbon atoms, an aryloxy group having 6 to 20 carbon atoms, a straight-chain, branched or cyclic alkylthio group having 1 to 10 carbon atoms, or an arylthio group having 6 to 20 carbon atoms; each pair of $A^1$ and $A^2$, $A^3$ and $A^4$, $A^5$ and $A^6$, and $A^7$ and $A^8$ may be bound together so as to form a ring; and Met represents two hydrogen divalent metal atom, a trivalent monosubstituted or tetravalent disubstituted metal atom, or an oxymetal group.

* * * * *